United States Patent
Miga et al.

(10) Patent No.: US 7,103,399 B2
(45) Date of Patent: Sep. 5, 2006

(54) APPARATUS AND METHODS OF CORTICAL SURFACE REGISTRATION AND DEFORMATION TRACKING FOR PATIENT-TO-IMAGE ALIGNMENT IN RELATION TO IMAGE-GUIDED SURGERY

(75) Inventors: Michael I. Miga, Franklin, TN (US); Benoit M. Dawant, Nashville, TN (US); Tuhin K. Sinha, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 3 days.

(21) Appl. No.: 10/936,339

(22) Filed: Sep. 8, 2004

(65) Prior Publication Data

US 2005/0148859 A1    Jul. 7, 2005

Related U.S. Application Data

(60) Provisional application No. 60/501,514, filed on Sep. 8, 2003.

(51) Int. Cl.
*A61B 5/05* (2006.01)

(52) U.S. Cl. .................. 600/425; 600/411; 600/417; 600/429

(58) Field of Classification Search .......... 600/425; 382/168–170, 128–131
See application file for complete search history.

(56) References Cited

U.S. PATENT DOCUMENTS

| | | | | |
|---|---|---|---|---|
| 5,078,141 A * | 1/1992 | Suzuki et al. | ............... | 600/422 |
| 5,836,872 A * | 11/1998 | Kenet et al. | ............... | 600/306 |
| 6,006,126 A * | 12/1999 | Cosman | ............... | 600/426 |
| 6,585,651 B1 * | 7/2003 | Nolte et al. | ............... | 600/449 |
| 6,858,826 B1 * | 2/2005 | Mueller et al. | ............... | 250/208.1 |

OTHER PUBLICATIONS

C. R. Maurer, J. M. Fitzpatrick, M. Y. Wang, R. L. Galloway, R. J. Maciumas, and G. S. Allen, "Registration of head volume images using implantable fiducial markers," *IEEE Trans. Med. Imag.*, vol. 16, pp. 447-462, Apr. 1997.

W. E. L. Grismon, G. J. Ettinger, S. J. White, T. Lozano Perez, W. M. Wells, and R. Kikinis, "An automatic registration method for frameless stereotaxy, image guided surgery, and enhanced reality visualization," *IEEE Trans. Med. Imag.*, vol. 15, pp. 129-140, Feb. 1996.

C. R. Maurer, R. J. Maciunas, and J. M. Fitzpatrick, "Registration of head CT images to physical space using a weighted combination of points and surfaces," *IEEE Trans. Med. Imag.*, vol. 17, pp. 753-761, May 1998.

M. A. Audette, K. Siddiqi, and T. M. Peters, "Level-set surface segmentation and fast cortical range image tracking for computing intra-surgical deformations," in *Lecture Notes in Computer Science.* New York: Springer-Verlag, 1999, vol. 1679, Medical Image Computing and Computer Assisted Intervention: MICCAI'99, pp. 788-797.

(Continued)

*Primary Examiner*—Brian L. Casler
*Assistant Examiner*—Julianne M. Sullivan
(74) *Attorney, Agent, or Firm*—Morris Manning & Martin; Tim Tingkang Xia, Esq.

(57) ABSTRACT

A cortical surface registration procedure related to a diagnostic or surgical procedure. In one embodiment, the procedure includes the steps of pre-operatively obtaining a first textured point cloud of the cortical surface of a targeted region of a brain of a living subject, intra-operatively obtaining optically a second textured point cloud of the cortical surface of the brain of the living subject, and aligning the first textured point cloud of the cortical surface to the second textured point cloud of the cortical surface so as to register images of the brain of the living subject to the cortical surface of the living subject.

13 Claims, 20 Drawing Sheets

OTHER PUBLICATIONS

A. Raabe, R. Krishman, R. Wolff, E. Hermann, M. Zimmermann, and V. Seifert, "Laser surface scanning for patient registration in intracranial image-guided surgery," *Neurosurgery*, vol. 50, No. 4, pp. 797-801, 2002.

M. A. Audette, F. P. Ferrie, and T. M. Peters, "An algorithmic overview of surface registration techniques for medical imaging," *Med. Image Anal.*, vol. 4, No. 3, pp. 201-217, 2000.

R. L. Galloway, "The process and development of image-guided procedures," *Annu. Rev. Biomed. Eng.*, vol. 3, pp. 83-108, 2001.

D. L. G. Hill, C. R. Maurer, R. J. Maciunas, J. A. Barwise, J. M. Fitzpatrick, and M. Y. Wang, "Measurement of intra-operative brain surface deformation under a craniotomy," *Neurosurgery*, vol. 43, No. 3, pp. 514-526, 1998.

D. W. Roberts, A. Hartov, F. E. Kennedy, M. I. Miga, and K. D. Paulsen, "Intra-operative brain shift and deformation: A quantitative analysis of cortical displacement in 28 cases," *Neurosurgery*, vol. 43, No. 4, pp. 749-758, 1998.

C. Nimsky, O. Ganslandt, S. Cerny, P. Hastreiter, G. Greiner, and R. Fahlbusch, "Quantification of, visualization of, and compensation for brain shift using intra-operative magnetic resonance imaging," *Neurosurgery*, vol. 47, No. 5, pp. 1070-1079, 2000.

A. Nabavi, P. M. Black, D. T. Gering, C. F. Westin, V. Mehta, R. S. Pergolizzi, M. Ferrant, S. K. Warfield, N. Hata, R. B. Schwartz, W. M. Wells, R. Kikinis, and F. A. Jolesz, "Serial intra-operative magnetic resonance imaging of brain shift," *Neurosurgery*, vol. 48, No. 4, pp. 787-797, 2001.

C. Nimsky, O. Ganslandt, H. Kober, M. Buchfelder, and R. Fahlbusch, "Intra-operative magnetic resonance imaging combined with neuronavigation: A new concept," *Neurosurgery*, vol. 48, No. 5, pp. 1082-1091, 2001.

W. E. L. Grimson, R. Kikinis, F. A. Jolesz, and P. M. Black, "Imageguided surgery," *Sci. Amer.*, vol. 280, No. 6, pp. 62-69, 1999.

C. Nimsky, O. Ganslandt, P. Hastreiter, and R. Fahlbusch, "Intra-operative compensation for brain shift," *Surg. Neurol.*, vol. 56, No. 6, pp. 357-364, 2001.

M. Knauth, N. Aras, C. R. Wirtz, A. Dorfler, T. Engelhorn, and K. Sartor, "Surgically induced intracranial contrast enhancement: Potential source of diagnostic error in intra-operative mr imaging," *Amer. J. Neuroradiol.*, vol. 20, No. 8, pp. 1547-1553, 1999.

G. R. Sutherland, T. Kaibara, C. Wallace, B. Tomanek, and M. Richter, "Intra-operative assessment of aneurysm clipping using magnetic resonance angiography and diffusion-weighted imaging: Technical case report," *Neurosurgery*, vol. 50, No. 4, pp. 893-897, 2002.

D. G. Gobbi, R. M. Comeau, and T. M. Peters, "Ultrasound/mri overlay with image warping for neurosurgery," in *Lecture Notes in Computer Science*. New York: Springer-Verlag, 2000, vol. 1935, Medical Image Computing and Computer-Assisted Intervention: MICCAI'00, pp. 106-114. (Manuscript Provided).

D. W. Roberts, M. I. Miga, A. Hartov, S. Eisner, J. M. Lernery, F. E. Kennedy, and K. D. Paulsen, "Intra-operatively updated neuroimaging using brain modeling and sparse data," *Neurosurgery*, vol. 45, No. 5, pp. 1199-1206, 1999.

M. I. Miga, K. D. Pausen, J. M. Lemery, S. D. Eisner, A. Hartov, F. E. Kennedy, and D. W. Roberts, "Model-updated image guidance: Initial clinical experiences with gravity-induced brain deformation," *IEEE Trans. Med. Imag.*, vol. 18, pp. 866-874, Oct. 1999.

M. I. Miga, K. D. Paulsen, F. E. Kennedy, P. J. Hoopes, A. Hartov, and D. W. Roberts, "In vivo analysis of heterogeneous brain deformation computations for model-updated image guidance," *Comput. Methods Biomech. Biomed. Eng.*, vol. 3, No. 2, pp. 129-146, 2000. (Manuscript Provided).

G. E. Christensen, R. D. Rabbitt, and M. I. Miller, "3D brain mapping using a deformable neuroanatomy," *Phys. Med. Biol.*, vol. 39, No. 3, pp. 609-618, 1994.

S. Nakajima, H. Atsumi, R. Kikinis, T. M. Moriarty, D. C. Metcalf, F. A. Jolesz, and P. M. Black, "Use of cortical surface vessel registration for image-guide neurosurgery," *Neurosurgery*, vol. 40, No. 6, pp. 1201-1208, 1997.

C. Studholme, D. L. G. Hill, and D. J. Hawkes, "An overlap invariant entropy measure of 3d medical image alignment," *Pattern Recognit.*, vol. 32, No. 1, pp. 71-86, 1999.

M. A. Biot, "General theory of three-dimensional consolidation," *Journal of Applied Physics*, vol. 12, pp. 155-164, 1941.

T. Nagashima, S. Takayuki, and S. I. Rapoport, "A two-dimensional, finite element analysis of vasogenic brain edema," *Neurol Med Chir* (Tokyo), vol. 30, pp. 1-9, 1990.

K. D. Paulsen, M. I. Miga, F. E. Kennedy, P. J. Hoopes, A. Hartov, and D. W. Roberts, "A computational model for tracking subsurface tissue deformation during stereotactic neurosurgery," *IEEE Transactions on Biomedical Engineering*, vol. 46, pp. 213-225, 1999.

M. Ferrant, A. Nabavi, B. Macq, P. M. Black, F. A. Jolesz, R. Kikinis, and S. K. Warfield, "Serial registration of intra-operative MR images of the brain," *Medical Image Analysis*, vol. 6, pp. 337-359, 2002.

P. J. Besl, and N.D. Mc Kay, "A method of registration of 3-D shapes," *IEEE Tran. On Pattern Analysis and Machine Intelligence* 14(2): 239-256. (1992).

O. Skrinjar, D. Spencer, and J. Duncan, "Brain shift modeling for use in neurosurgery," in *Medical Image Computing and Computer-Assisted Intervention—Miccai'98*, vol. 1496, *Lecture Notes in Computer Science*, pp. 641-649, 1998. (Manuscript Provided).

C. Davatzikos, D. G. Shen, A. Mohamed, and S. K. Kyriacou, "A framework for predictive modeling of anatomical deformations," *IEEE Transactions on Medical Imaging*, vol. 20, pp. 836-843, 2001.

A. E., Johnson S. B. Kang Registration and intergration of textured 3D data. *Image and Vision Computing* 17(2): 135-147, (1999).

T.K. Sinha, D. M. Cash, R. J. Weil, R. L. Galloway, M. I. Miga, "*Cortical Surface Registration Using Texture Mapped Point Clouds and Mutual Information*" Lecture Notes in Computer Science: Medical Image Computing and Computer-Assisted Intervention—MICCAI 2002, Springer Verlag, New York, vol. 2488, Part 2, pp. 533-540, 2002 (Manuscript Provided).

T. K. Sinha, D. M. Cash, R. J. Weil, R. L. Galloway, M. I. Miga. "*Textured Laser Range Scanning and Registration of the Cortical Surface,*" 24th *Annual International Conf. Of EMBS and BMES*, 2002. (Manuscript Provided).

M. I. Miga, T. K. Sinha, D. M. Cash, R. L. Galloway, and R. J. Weil, "Cortical Surface Registration for Image-Guided Neurosurgery Using Laser-Range Scanning," *IEEE Transactions on Medical Imaging*, vol. 22, No. 8, pp. 973-985, 2003. (Manuscript Provided).

V. Duay, T. K. Sinha, P. D'Haese, M. I. Miga, B. M. Dawant, "Non-Rigid Registration of Serial Intra-Operative Images For Automatic Brain-Shift Estimation," Lecture Notes in Computer Science: Second International Workshop on Biomedical Image Registration—WBIR 2003, vol. 2717, pp. 61-70, 2003. (Manuscript Provided).

T.K. Sinha, D. M. Cash, R. J. Weil, R. L. Galloway, M. I. Miga, "*Laser Range Scanning for Cortical Surface Characterization During Neurosurgery,*" Medical Imaging 2003: Visulization, Image-guided Procedures, and Display: Proc. Of the SPIEvol. 5029, pp. 98-107 (Manuscript Provided).

H. J. Nauta, "Error assessment during "image guided" and "imaging interactive" stereotactic surgery," *Comput. Med. Imag. Graphics*, vol. 18, No. 4, pp. 279-287, 1994.

P. Dumpuri, R. C. Chen, M. I. Miga, "Model Updated Image Guidence: A Statistical Approach", Lecture Notes in Computer Science: Medical Image Computing and Computer-Assisted Intervention—MICCAI 2003, vol. 2879, Part 1, pp. 375-382, 2003.

Michel A. Audette, Kaleem Siddiqui, Frank P. Ferrie, and Terry M. Peters, "*An Integrated Range-Sensing, Segmentation And Registration Framework For The Characterization Of Intra-Surgical Brain Deformations In Image-Guided Surgery*", Computer Vision and Image Understanding, vol. 89, pp. 226-251, 2003.

\* cited by examiner (c)

(b)

(a)

APPARATUS AND METHODS OF CORTICAL SURFACE REGISTRATION AND DEFORMATION TRACKING FOR PATIENT-TO-IMAGE ALIGNMENT IN RELATION TO IMAGE-GUIDED SURGERY

CROSS-REFERENCE TO RELATED PATENT APPLICATION

This application claims the benefit, pursuant to 35 U.S.C. §119(e), of provisional U.S. patent application Ser. No. 60/501,514, filed Sep. 8, 2003, entitled "APPARATUS AND METHODS OF CORTICAL SURFACE REGISTRATION AND DEFORMATION TRACKING FOR PATIENT-TO-IMAGE ALIGNMENT DURING IMAGE-GUIDED SURGERY," by Michael I. Miga, Benoit M. Dawant and Tuhin K. Sinha, which is incorporated herein by reference in its entirety.

STATEMENT OF FEDERALLY-SPONSORED RESEARCH

This invention was made in part with U.S. Government support under Grant NIH/NCI IR21 CA89657-01A2, awarded by the National Institute of Health. The U.S. Government may have certain rights in this invention.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference. In terms of notation, hereinafter, "[n]" represents the nth reference cited in the reference list. For example, [28] represents the 28th reference cited in the reference list, namely, M. I. Miga, K. D. Paulsen, J. M. Lemery, S. D. Eisner, A. Hartov, F. E. Kennedy, and D. W. Roberts, "Model-updated image guidance: Initial clinical experiences with gravity-induced brain deformation," *IEEE Trans. Med. Imag.*, vol. 18, pp. 866–874, October 1999.

FIELD OF THE INVENTION

The present invention generally relates to image-guided surgery, and in particular to apparatus and methods of cortical surface registration and/or deformation tracking for patient-to-image alignment in relation to image-guided surgery.

BACKGROUND OF THE INVENTION

Image-guided surgery (hereinafter "IGS") involves a patient-specific anatomical image pre-operatively acquired that spatially localizes pathology, digitization technology that allows the identification and tracking of targeted points of interest in a patient's physical space in an operating room (hereinafter "OR"), and alignments of the patient-specific images to the patient's physical space in the OR such tat the digitization technology can be referenced the patient-specific images and used for guidance during surgery. Central to the IGS is the method of registering an image space (a coordinate system corresponding to the pre-operative images) to a physical space (a coordinate system corresponding to the intra-operative anatomy of the patient). Once the registration is performed, all pre-operative planning and acquired data related to the patient's anatomy could be displayed intra-operatively to a surgeon and used for assistance in surgical guidance and treatment.

Over the past years, a variety of registration methods have been developed. Among them, a point-based registration (hereinafter "PBR") has been mostly characterized and thoroughly examined, whereby landmarks are localized in patient's image volumes and aligned with corresponding landmarks digitized in physical space of the patient intra-operatively. The landmarks, or fiducials, can be either natural structures such as a nose bridge of the patient or synthetic components such as small cylindrical markers adhered to the skin of the patient or markers implanted into the skull of the patient prior to image acquisitions [1, 2]. Further analysis of configurations of fiducial markers, optimum marker numbers, and effects on target localization error has been reported [2]. The PBR technique has proven clinically accurate and useful. However, utilization of the PBR method requires a preliminary surgery for implantation of the fiducial markers to predetermined positions in a patient's anatomy.

Another technique for the registration is accomplished by identifying two geometric surfaces that are the same in an image space and a physical space of a patient, respectively, and aligning them between the two spaces. The ability to acquire surface data using a probe, such as optical probe, electromagnetic probe, and/or ultrasound probe, and lasers [3–7] in conjunction with surface extraction algorithms applied to imaging data has led to new methods of surface based registrations [8]. The primary difference between the surface-based registration and the PBR is that the surface based registration does not require a one-to-one point correspondence. On the other hand, an averaging effect in the surface-based registration serves to reduce uncorrelated localization error generated during the acquisition of spatially well-resolved surface data. However, the surface based alignment techniques are limited with facts, for example, scalps lack geometric specificity, and skin surfaces may deform due to intra-operative drugs or procedural retraction [9]. An alternative registration technique, less commonly used for IGS purposes, is an intensity-based or volume registration approach [2], which is usually applied for alignments of a source image volume to a target image volume.

However, recent studies have shown limitations in accuracy with current image-guided procedures. The discrepancy observed is a by-product of the rigid-body assumptions and techniques used during the registration process. Specifically, with neurosurgery, registration is provided by markers attached to the skull of a patient or on the skin surrounding the skull of a patient, where soft-tissue deformations of the brain during surgery may result in significant errors in aligning a pre-operative image space to an actual physical space. One of the earliest observed instances of the error was reported by Kelly et al. [10]. More recently, Nauta has measured this shift that is of an order of 5 mm [11]. Subsequent investigations in intra-operative brain surface movements have shown that an average deformation for brain shifts is about 1 cm. Moreover, predispositions for brain movement in the direction of gravity have been investigated [12,13].

This has lead studies to develop methods and techniques that can compensate for intra-operative brain shifts. One of the methods includes the use of conventional imaging modalities during surgery, i.e. intra-operative computed tomography (hereinafter "iCT"), intra-operative magnetic resonance (hereinafter "iMR"), and/or intra-operative ultrasound (hereinafter "iUS") imaging. When available, intra-operative images are registered to pre-operative images using a number of nonrigid intra-modal and/or inter-modal registration methods. In the 1980s, there was a significant effort to incorporate iCT during surgery as a means for acquiring intra-operative image series. However, dose considerations of repeatedly using computed tomography (hereinafter "CT") scanning in the OR have hindered adoption of the iCT technique [14]. More recently, several medical centers have explored the use of iMR imaging for data acquisition and shift compensation [15–18] and have developed elegant and sophisticated methods for visualization in the OR [3, 19, 20]. Although conceptually appealing, the exorbitant cost and cumbersome nature of such a system (e.g., need for a MR compatible OR) have left their widespread adoption uncertain. In addition to these logistical concerns, recent reports have demonstrated potential problems related to surgically induced contrast enhancement that could be often confused with contrast-enhancing residual tumor [21], and image distortions from susceptibility and/or eddy current artifacts related to the presence of MR compatible Yasargil clips for aneurysm clipping procedures [22]. An alternative to iCT and iMR imaging is the use of iUS [23–26], where locally reconstructed iUS image volumes may provide a real-time guidance feedback. However, the quality of the iUS images over the course of surgery limits their effectiveness in shift compensation.

A possible alternative to high-cost intra-operative imaging is to use computational methods to compensate for brain shifts in IGS. A strategy for using computational methods to correct for brain shifts in neurosurgery was highlighted by Roberts et al. [27]. Rapidly acquiring minimally invasive data that describes changes in brain geometry during surgery is necessary to develop a computational approach that accounts for brain deformations. In these methods, intra-operative surface data are combined with a statistical and/or mathematical model of the soft-tissue mechanics that describe brain deformation [27]. Physical models have been successfully used to reconstitute 75% to 85% of the shift occurring under loads similar to a clinical setting. A detailed work regarding the fidelity of such computations within animal and human systems has been reported [28, 29]. Registrations of multimodality images by elastic matching technique have also been studied [30, 31]. Deformable templates for large deformation warping of images have been utilized [32]. However, the computational methods may not be able to effectively predict the extent of tumor margins.

Therefore, a heretofore unaddressed need exists in the art to address the aforementioned deficiencies and inadequacies.

SUMMARY OF THE INVENTION

In one aspect, the present invention relates to a method of registering an image volume of a brain of a living subject to a cortical surface of at least one targeted region of the brain of the living subject. In one embodiment, the method includes the step of pre-operatively acquiring the image volume from the brain of the living subject, wherein the image volume of the brain of the living subject comprises image data with respect to the brain surface geometry. The image data with respect to the brain surface geometry, in one embodiment, is obtained through the use of at least one of positron emission tomography, electroencephalography, computer tomography, functional magnetic resonance imaging and magnetic resonance imaging.

The method further includes the step of generating a grayscale encoded brain surface from the acquired image volume. In one embodiment, the generating step comprises the steps of segmenting the acquired image volume of the brain of the living subject, extracting a point cloud representation of the brain surface geometry from the segmented image volume, and performing a ray-casting and voxel intensity averaging on the point cloud representation so as to generate a grayscale encoded brain surface that contains intensity patterns representing sulcal-gyrus differences and contrast-enhanced vasculature.

Furthermore, the method includes the step of intra-operatively obtaining a textured point cloud of the cortical surface of the at least one targeted region of the brain of the living subject. The step of obtaining a textured point cloud of the cortical surface is performed with an optical device that is capable of obtaining frequency, intensity and geometric data with respect to the cortical surface simultaneously. In one embodiment, the optical device is a laser range scanner (hereinafter "LRS"). The step of intra-operatively obtaining a textured point cloud of the cortical surface comprises the steps of optically scanning an exposed brain surface of the living subject during surgery with the laser range scanner, capturing surface-reflected light from the brain surface of the living subject, acquiring a point cloud representation of the geometry of the cortical surface from the captured surface-reflected light, and color-encoding the acquired point cloud representation with intensity values of a field of view so as to obtain a textured point cloud of the cortical surface of the at least one targeted region of the brain.

Moreover, the method includes the step of aligning the grayscale-encoded brain surface to the textured point cloud of the cortical surface so as to register the image volume of the brain with respect to the cortical surface of the at least one targeted region of the brain. In one embodiment, the step of aligning the grayscale-encoded brain surface to the textured point cloud of the cortical surface comprises the steps of registering the grayscale-encoded brain surface of the brain to the textured point cloud of the cortical surface of the targeted region of the brain using an iterative closest point algorithm, and optimizing the grayscale-encoded brain surface of the brain to the textured point cloud of the cortical surface of the targeted region of the brain using normalized mutual information. In one embodiment, the registering step includes the steps of pairing corresponding points from the grayscale-encoded brain surface of the brain and the textured point cloud of the cortical surface of the targeted region of the brain according to a closest distance metric, executing a point-based registration, updating the closest distance metric accordingly, and repeating the pairing step, the executing step and the updating step until a disparity function d satisfies a specified tolerance, wherein the disparity function d has the form of $$d = \frac{1}{N}\sum_{j}^{N} \|y_j - T(x_j)\|^2,$$

where $T(x_j)$ represents a rigid transformation of N points on a source surface to corresponding points on a target surface, $y_j$. The optimizing step, in one embodiment, comprises the steps of choosing a normalized mutual information in the form of $$NMI(x, y) = \frac{H(x) + H(y)}{H(x, y)},$$

where H(x) and H(x, y) are the marginal and joint entropies of the point clouds, respectively, using the closest distance metric to determine proper intensity correspondence among a source surface and a target surface, fitting a spherical geometry to reduce the registration degrees of freedom, and optimizing the normalized mutual information using an iterative procedure.

In another aspect, the present invention relates to a cortical surface registration procedure related to a diagnostic or surgical procedure. In one embodiment, the cortical surface registration procedure includes the steps of pre-operatively obtaining a first textured point cloud of the cortical surface of a targeted region of a brain of a living subject, intra-operatively obtaining optically a second textured point cloud of the cortical surface of the brain of the living subject, and aligning the first textured point cloud of the cortical surface to the second textured point cloud of the cortical surface so as to register images of the brain of the living subject to the cortical surface of the living subject.

In one embodiment, the step of pre-operatively obtaining a first textured point cloud comprises the steps of pre-operatively acquiring an image volume from the brain of the living subject, segmenting the acquired image volume, extracting a point cloud representation of the brain surface geometry from the segmented image volume, performing a ray-casting and voxel intensity averaging on the point cloud representation so as to generate a grayscale encoded brain surface that contains intensity patterns representing sulcal-gyrus differences and contrast-enhanced vasculature, and obtaining the first point cloud from the grayscale encoded brain surface.

Furthermore, the step of intra-operatively obtaining optically a second textured point cloud includes the steps of optically scanning an exposed brain surface of the living subject during surgery, capturing surface-reflected light from the brain surface of the living subject, acquiring a point cloud representation of the geometry of the cortical surface from the captured surface-reflected light, and color-encoding the acquired point cloud representation with intensity values of a field of view so as to obtain the second textured point cloud of the cortical surface of the at least one targeted region of the brain.

Additionally, the step of aligning the first textured point cloud of the cortical surface to the second textured point cloud of the cortical surface comprises the steps of registering the first textured point cloud of the cortical surface to the second textured point cloud of the cortical surface using an iterative closest point algorithm, and optimizing the first textured point cloud of the cortical surface to the second textured point cloud of the cortical surface using normalized mutual information.

In yet another aspect, the present invention relates to a system for cortical surface registration related to a diagnostic or surgical procedure. In one embodiment, the system has an imaging acquiring device for pre-operatively obtaining a first textured point cloud of the cortical surface of a targeted region of a brain of a living subject, an optical device for intra-operatively obtaining a second textured point cloud of the cortical surface of the brain of the living subject, and a computer for receiving and processing data related to the first textured point cloud of the cortical surface and the second textured point cloud of the cortical surface so as to register images of the brain of the living subject to the cortical surface of the living subject. The system further includes a display device coupled to the computer for displaying the cortical surface registration dynamically to facilitate the diagnostic or surgical procedure.

In one embodiment, the imaging acquiring device includes at least one of positron emission tomography device, electroencephalography device, computer tomography device, functional magnetic resonance imaging device and magnetic resonance imaging device. The optical device comprises a laser device. In one embodiment, the laser device is a laser range scanner adapted for optically scanning an exposed brain surface of the living subject during the diagnostic or surgical procedure. Furthermore, the optical device includes a first digital camera adapted for capturing surface-reflected light from the brain surface of the living subject when the brain surface of the living subject is scanned by the laser range scanner. Moreover, the optical device includes a second digital camera adapted for capturing an image of the surgical field of view.

In a further aspect, the present invention relates to a method of deformable cortical surface registration related to a diagnostic or surgical procedure to track brain deformation. In one embodiment, the method includes the steps of obtaining a first three-dimensional (hereinafter "3D") point cloud of a brain of a living subject prior to or during brain deformation, where each 3D point of the first 3D point cloud is color-encoded, generating a first two-dimensional (hereinafter "2D") photographic image from the first 3D point cloud, obtaining a second 3D point cloud of the brain during or after brain deformation, wherein each 3D point of the second 3D point cloud representation is color-encoded, generating a second 2D photographic image from the second 3D point cloud, and non-rigidly aligning the first 2D photographic image and the second 2D photographic image so as to track the brain deformation.

In one embodiment, the step of obtaining a first 3D point cloud comprises the steps of optically scanning an exposed brain surface of the living subject at a time prior to or during brain deformation, capturing surface-reflected light from the brain surface of the living subject, acquiring a first point cloud representation of the geometry of the cortical surface from the captured surface-reflected light, and color-encoding the acquired each point of the first point cloud representation by a direct linear transform representation so as to construct the first 3D point cloud. The step of optically scanning an exposed brain surface, in one embodiment, is performed with an optical device that is capable of obtaining frequency, intensity and geometric data with respect to the cortical surface simultaneously, wherein the optical device is a laser range scanner.

The step of obtaining a second 3D point cloud includes the same steps as obtaining the first 3D point cloud, but the step is performed during or after the step of obtaining the first 3D point cloud.

Additionally, the step of non-rigidly aligning the first 2D photographic image and the second 2D photographic image so as to track the brain deformation includes the steps of transforming the first and second 2D photographic images from RGB images into corresponding gray level images, and obtaining a final deformation field that registers gray level images one to the other. In one embodiment, the step of obtaining a deformation field comprises the steps of calculating a deformation field for each of a series of levels, wherein each level is corresponding to a particular combination of scale and resolution for an image, and adding all the deformation fields for all of the series of levels to generate the final deformation field.

In yet a further aspect, the present invention relates to a system of deformable cortical surface registration related to a diagnostic or surgical procedure to track brain deformation. In one embodiment, the system has image data acquiring means for obtaining a first 3D point cloud of a brain of a living subject prior to or during brain deformation, where each 3D point of the first 3D point cloud is color-encoded, and a second 3D point cloud of the brain during or after brain deformation, where each 3D point of the second 3D point cloud representation is color-encoded, respectively. The image data acquiring means is capable of optically scanning an exposed brain surface of the living subject at a selected time, capturing surface-reflected light from the brain surface of the living subject, acquiring a point cloud representation of the geometry of the cortical surface from the captured surface-reflected light, and color-encoding the acquired each point of the point cloud representation by a direct linear transform representation so as to construct a 3D point cloud. In one embodiment, the image data acquiring means includes an optical device that is capable of obtaining frequency, intensity and geometric data with respect to the cortical surface simultaneously. The optical device, in one embodiment, is a laser range scanner. Furthermore, the image data acquiring means includes a first digital camera adapted for capturing surface-reflected light from the brain surface of the living subject when the brain surface of the living subject is scanned by the laser range scanner. Additionally, the image data acquiring means comprises a second digital camera adapted for capturing an image of the surgical field of view.

Furthermore, the system has image generating means for generating a first 2D photographic image from the first 3D point cloud, and a second 2D photographic image from the second 3D point cloud, respectively, and registration means for non-rigidly aligning the first 2D photographic image and the second 2D photographic image so as to track the brain deformation. In one embodiment, the image generating means comprises a computer. The registration means comprises a controller.

These and other aspects of the present invention will become apparent from the following description of the preferred embodiment taken in conjunction with the following drawings, although variations and modifications therein may be affected without departing from the spirit and scope of the novel concepts of the disclosure.

These and other aspects of the present invention will become apparent from the following description of the preferred embodiment taken in conjunction with the following drawings, although variations and modifications therein may be affected without departing from the spirit and scope of the novel concepts of the disclosure.

DETAILED DESCRIPTION OF THE INVENTION

Figure 1:
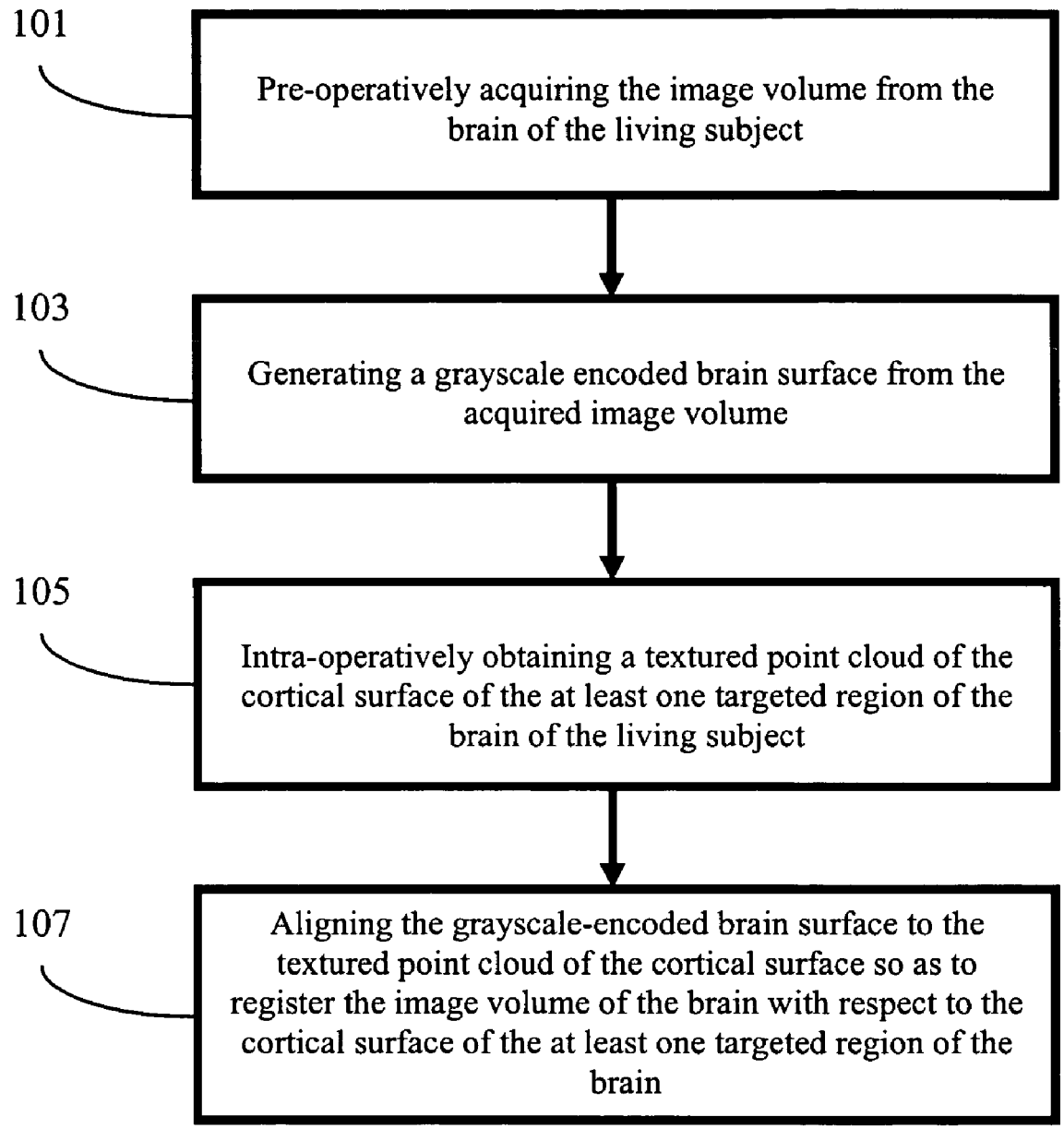
FIG. 1 is a flowchart for registering an image volume of a brain of a living subject to a cortical surface of at least one targeted region of the brain of the living subject according to one embodiment of the present invention.

The present invention is more particularly described in the following examples that are intended as illustrative only since numerous modifications and variations therein will be apparent to those skilled in the art. Various embodiments of the invention are now described in detail. Referring to the drawings, like numbers indicate like parts throughout the views. As used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which has no influence on the scope of the invention. Additionally, some terms used in this specification are more specifically defined below.

DEFINITIONS

The terms used in this specification generally have their ordinary meanings in the art, within the context of the invention, and in the specific context where each term is used.

Certain terms that are used to describe the invention are discussed below, or elsewhere in the specification, to provide additional guidance to the practitioner in describing various embodiments of the invention and how to practice the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term. Likewise, the invention is not limited to various embodiments given in this specification.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, the term "living subject" refers to a human being such as a patient, or an animal such as a lab testing monkey.

As used herein, the term "field of view" (hereinafter "FOV") refers to an extent of a visible image field of a region of interest of a living subject under treatment or test.

As used herein, "registration," and "alignment" are synonyms in the specification.

OVERVIEW OF THE INVENTION

Figure 2:
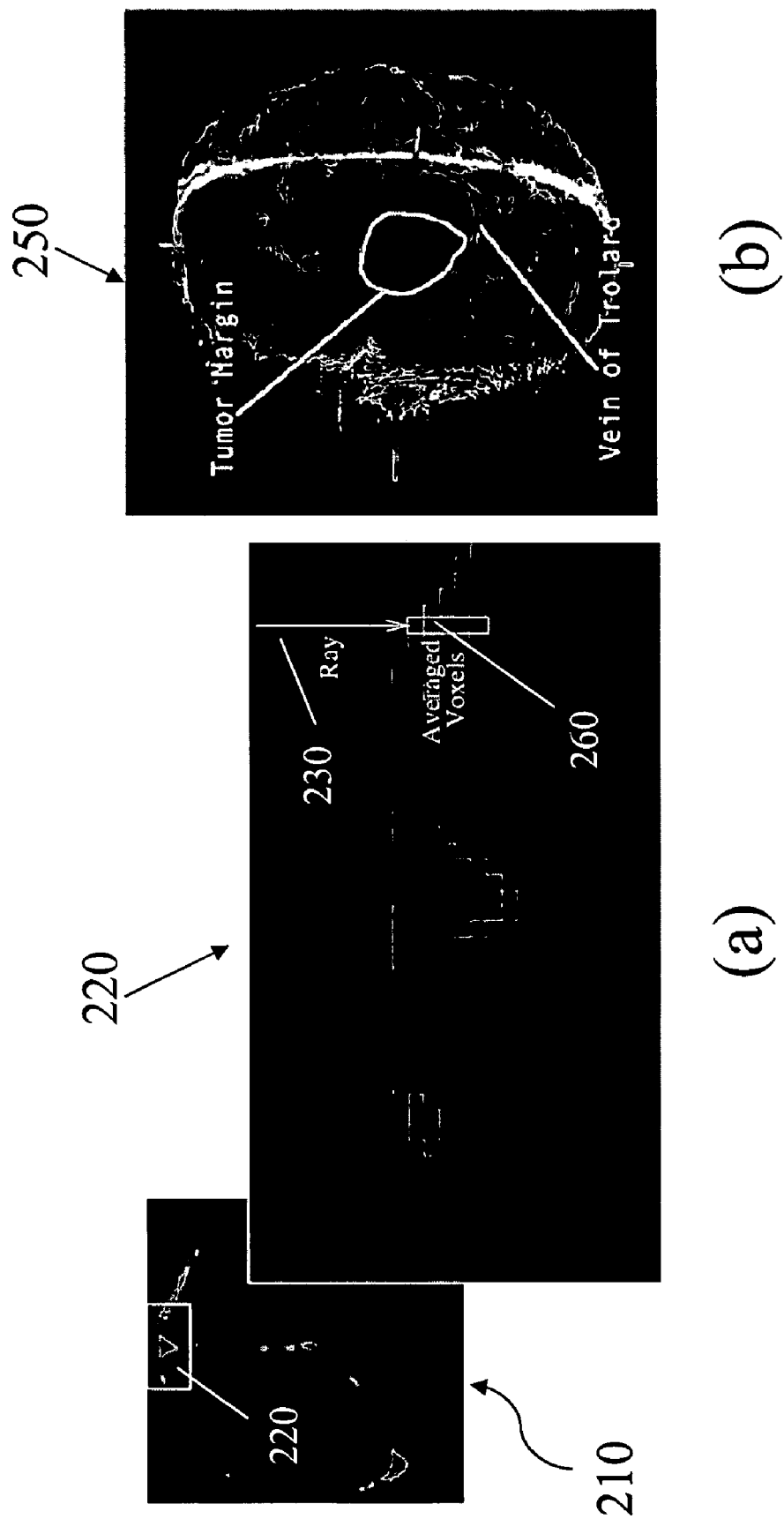
FIG. 2 shows a texture mapping process for generating a grayscale encoded cortical brain surface from a pre-operative MR image volume: (a) a ray-casting and voxel averaging algorithm applied to a segmented pre-operative MR brain volume, and (b) a resultant grayscale encoded cortical brain surface (i.e., textured point cloud) from the segmented pre-operative MR brain volume.
Figure 3:
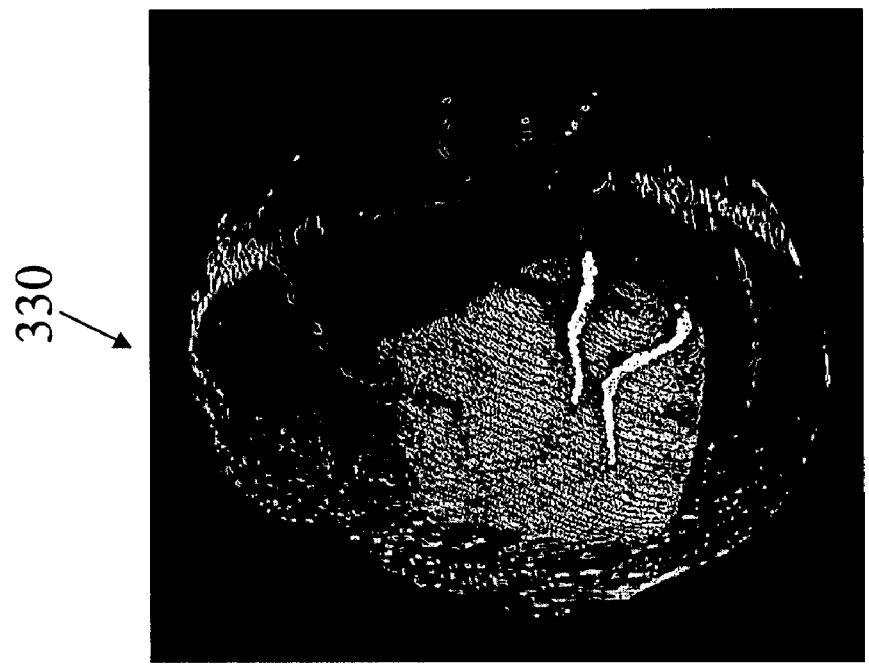
FIG. 3 shows a cortical surface registration according to one embodiment of the present invention: (a) a grayscale encoded cortical brain surface generated from a pre-operative MR image volume of a living subject, (b) a textured point cloud intra-operatively acquired by a laser range scanner from a targeted region of interest of the living subject, and (c) an alignment of the textured point cloud to the grayscale encoded cortical brain surface.
Figure 3:
Figure 3:
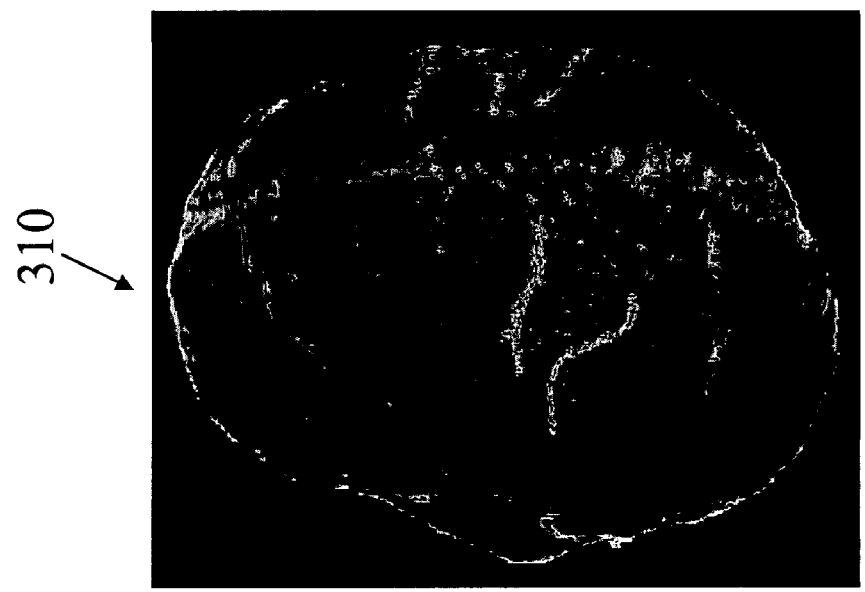

The present invention, in one aspect, relates to a method of registering an image volume of a brain of a living subject to a cortical surface of at least one targeted region of the brain of the living subject. Referring to FIGS. 1–3 and first to FIG. 1, the method, in one embodiment, includes the following steps: at step 101, the image volume is acquired pre-operatively from the brain of the living subject, where the image volume of the brain of the living subject comprises image data with respect to the brain surface geometry. The image data with respect to the brain surface geometry, in one embodiment, is obtained through the use of at least one of positron emission tomography (hereinafter "PET"), electroencephalography, computer tomography, functional magnetic resonance (hereinafter "fMR") imaging and magnetic resonance imaging.

At step 103, a grayscale encoded brain surface is generated from the acquired image volume. In one embodiment, the generating step comprises the steps of segmenting the acquired image volume of the brain of the living subject, extracting a point cloud representation of the brain surface geometry from the segmented image volume, and performing a ray-casting and voxel intensity averaging on the point cloud representation so as to generate a grayscale encoded brain surface that contains intensity patterns representing sulcal-gyrus differences and contrast-enhanced vasculature.

Referring now to FIG. 2, a location of a resection surface on a MR image 210 pre-operatively acquired from a brain of a patient is identified, for example, surface 220, according to a pre-operative surgical plan. The MR image volume 210 is segmented and the surface 220 of the segmented MR image volume is shown in FIG. 2a. From the segmented MR image volume, a point cloud representation of the brain surface geometry is extracted. Specifically, the surface 220 of the segmented MR image volume is positioned orthogonal to a ray-casting source having a ray 230. A ray-casting algorithm combined with voxel intensity averaging 260 is employed to grayscale encode the point cloud. In one embodiment, the voxel intensity averaging process averages 3 to 5 voxel intensities along the ray 230. At the conclusion of this process, the patient's cortical image surface is rendered into a textured point cloud 250 that contains intensity patterns representing sulcal-gyrus differences as well as contrast-enhanced vasculature, as shown in FIG. 2b. For the point clouds generated via the ray casting algorithm, the mean and median point-to-point distances are 0.7 and 0.6 mm, respectively.

Referring back to FIG. 1, at step 105, a textured point cloud of the cortical surface is obtained intra-operatively from the at least one targeted region of the brain of the living subject. The step of obtaining a textured point cloud of the cortical surface is performed with an optical device that is capable of obtaining frequency, intensity and geometric data with respect to the cortical surface simultaneously. In one embodiment, the optical device is a LRS, for example, RealScan3D, (3D Digital Corporation, Bedford Hills, N.Y.). The ability to rapidly capture both geometric and color-intensity information from an intra-operative brain surface has made a laser range scanner, in conjunction with cortical surface registrations, to be a very promising tool for tracking of brain deformation. For example, Nakajima et al. [33] has demonstrated an average of 2.3±1.3 mm fiducial registration error using cortical vessels scanned with a LRS for registration. Also, some preliminary work using a scanning based system for cortical surface geometric registration has been reported but a systematic evaluation has not been performed to date [5]. Great clinical relevance would be gained if geometric and intensity information from an intra-operative brain surface could be invasively captured and effectively aligned to a pre-operative patient-specific image so as to track brain deformation for guidance during surgery. The LRS is capable of optically scanning an exposed brain surface of the living subject during surgery with a laser, capturing surface-reflected light from the brain surface of the living subject, acquiring a point cloud representation of the geometry of the cortical surface from the captured surface-reflected light, and color-encoding the acquired point cloud representation with intensity values of a field of view so as to obtain a textured point cloud of the cortical surface of the at least one targeted region of the brain.

With respect to an intra-operative acquisition of data, a calibration object is routinely scanned prior to registration so as to ensure operational fidelity of the LRS. At select times during the surgery, after durotomy, the LRS is positioned over the exposed brain surface and operated by passing a laser stripe continuously over the exposed brain surface in approximately 5–7 seconds. The laser output is detected by a first digital camera such as a high resolution charge-coupled device (hereinafter "CCD") camera of the LRS and principles of triangulation are used to determine the 3D location of each illuminated point so as to construct the point cloud. Following the laser-stripe pass, a second color CCD camera of the LRS is used to acquire a red-green-blue (hereinafter "RGB") bitmap image of the surgical FOV, which is used to color-encode each 3D point so as to obtain the textured point cloud of the surgical FOV. The mean and median point-to-point distances for the range-scan point clouds are 0.65 and 0.6 mm, respectively.

At step 107, the grayscale-encoded brain surface is aligned to the textured point cloud of the cortical surface so as to register the image volume of the brain with respect to the cortical surface of the at least one targeted region of the brain. FIG. 3 shows the alignment 330 of the grayscale-encoded brain surface 310 to the textured point cloud 320 of the cortical surface. In one embodiment, the alignment of the grayscale-encoded brain surface to the textured point cloud of the cortical surface is carried out by registering the grayscale-encoded brain surface of the brain to the textured point cloud of the cortical surface of the targeted region of the brain using an iterative closest point (hereinafter "ICP") algorithm.

The registration, in one embodiment, includes the following steps: (a) corresponding points from the grayscale-encoded brain surface of the brain and the textured point cloud of the cortical surface of the targeted region of the brain are paired according to a closest distance metric, (b) a point-based registration is executed, (c) the closest distance metric is updated accordingly. And then steps (a)–(c) are repeated until a disparity function d satisfies a specified tolerance, wherein the disparity function d has the form of:

$$d = \frac{1}{N}\sum_{j}^{N} \|y_j - T(x_j)\|^2, \quad (1)$$

where $T(x_j)$ represents a rigid transformation of a point, $x_j$, on a source surface such as the grayscale-encoded brain surface to a corresponding point, $y_j$, on a target surface such as the textured point cloud of the cortical surface, and N is the number of points in the source surface. The mean residual distance between counter points in each of the grayscale-encoded brain surface and the textured point cloud of the cortical surface is used as the closest distance metric of registration accuracy. To calculate this metric, correspondence between target cloud counter points and transformed source cloud counter points is established via nearest neighbor calculation. Mean registration error (hereinafter "MRE") is defined by a disparity function (1).

Although excellent at aligning geometrically unique surfaces, ICP registration generally has difficulty with an intra-operative environment if relied upon solely. In reality, not all regions of the brain surface can be expressed as a unique geometry with respect to visible sulcal/fissure features of the intra-operatively exposed brain. Pathology, such as a tumor, can also influence the initial shape of the brain surface dramatically. In addition, the fidelity of image segmentation can also become a potential source of misalignment. Thus, a necessary step of the alignment of the two point clouds is to optimize the ICP registration.

The optimization of the ICP registration according to one embodiment is to normalize or optimize the mutual information (hereinafter "MI") of the two point clouds, which includes the step of choosing a normalized mutual information (hereinafter "NMI") in the form [34] of $$NMI(x, y) = \frac{H(x) + H(y)}{H(x, y)}, \quad (2)$$

where H(x) and H(x, y) are the marginal and joint entropies of the point clouds, respectively. In addition, the closest distance metric is used to determine proper intensity correspondence between a source surface and a target surface. To aid the optimization process, the source cloud is constrained to move along the surface of a sphere fitted to the target cloud. The constraint reduces the degrees of freedom from six in Cartesian coordinates (position and orientation) to three in sphere coordinates (azimuth, elevation and roll). Finally, the normalized mutual information is optimized by using an iterative procedure. In one embodiment, the iterative procedure includes the Powell's iterative method [35].

The registration algorithm of the present invention is referred to a SurfaceMI registration in the specification.

In another aspect, the present invention relates to a system for cortical surface registration related to a diagnostic or surgical procedure. The system, in one embodiment, has an imaging acquiring device for pre-operatively acquiring an image volume of a targeted region of a brain of a living subject from which a first textured point cloud of the cortical surface, for example, a grayscale encoded brain surface, is derived. A conventional imaging scanner for obtaining one of PET, electroencephalography, CT, fMR and MR images can be used to practice the invention.

One critical component in the system for cortical surface registration related to a diagnostic or surgical procedure is a rapid acquisition of geometric data that describes the deforming nature of the brain during surgery. A LRS, for example, RealScan3D, is capable of capturing 3D topography of a target of interest as well surface texture mapping to submillimeter accuracy.

The RealScan3D is lightweight, compact, and has a standard tripod mount with a volume 9.5"×12.5"×3.25" and weight 4.5 lbs. For a clinical use, the RealScan3D is equipped with a customized vibration-damping monopod, and/or attached to a surgical arm within the OR. The scanning field of the RealScan3D has 512 horizontal points by 500 vertical points per scan and is accomplished in approximately 5 s to 7 s. The laser used in the LRS is a Class-I "eye-safe" 6.7 mW visible laser. The laser stripe generator has an adjustable fan-out angle (maximum fan-out is 30°) and acquires each stripe at approximately 60 Hz. The LRS accuracy is 300 µm at a position that is 30 cm far from a targeted region of interest and approximately 1000 µm at a position that is 80 cm far from the targeted region of interest.

In one embodiment, the LRS is brought to between 30 cm to 45 cm of the target. The complete process of moving the LRS into the field of view (hereinafter "FOV"), acquiring a scan, and exiting from the FOV takes approximately 1 to 1.5 min, which includes laser light and fan-out angle adjustments. In general, an impact of the LRS on the OR is negligible. The LRS is actively tacked in the OR space using a spatial tracking system, such as OPTOTRAK® 3020, (Northern Digital, Inc., Waterloo, Canada), and calibrated using phantoms with separate independent digitization. Additionally, prior to clinical data acquisition, the use of the LRS on human patients is approved by the Vanderbilt University Institutional Review Board (hereinafter "VUIRB") and patient consent is acquired for all clinical data.

The system also has a computer for receiving and processing data related to the first textured point cloud of the cortical surface and the second textured point cloud of the cortical surface so as to register images of the brain of the living subject to the cortical surface of the living subject. The system further includes a display device coupled to the computer for displaying the cortical surface registration dynamically to facilitate the diagnostic or surgical procedure. Any type of computers, such as personal computer, laptop, and supercomputer, and displays, such as display monitor, and liquid crystal display, can be employed to practice the current invention.

In a further aspect, the present invention relates to a method of deformable cortical surface registration related to a diagnostic or surgical procedure to track brain deformation.

Figure 4:
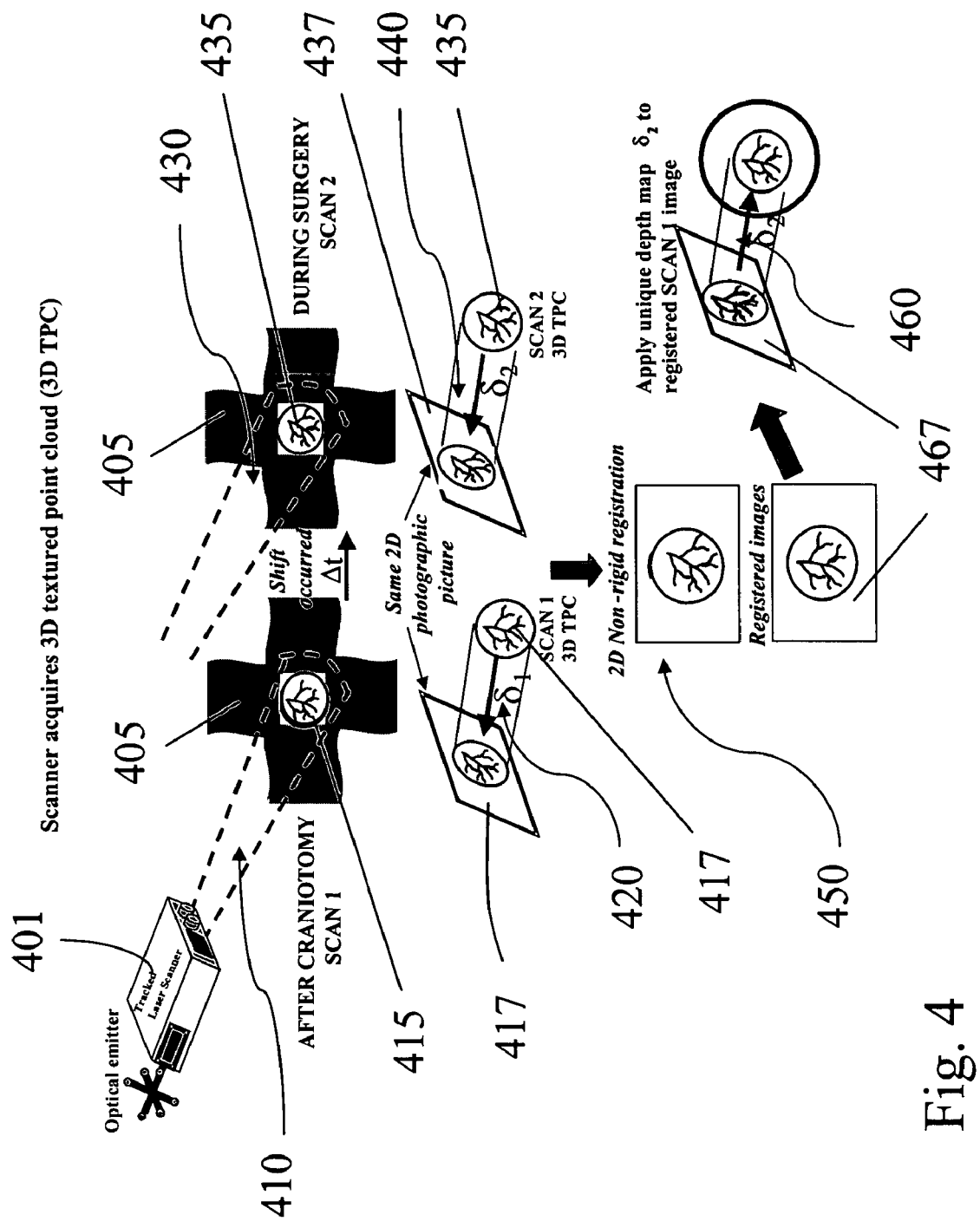
FIG. 4 shows a schematic framework for tracking brain shift using a laser range scanner according one embodiment of the present invention.

Referring to FIG. 4, the method according to one embodiment of the present invention includes the following steps: at step 410, a first 3D point cloud 415 of a brain of a living subject is obtained prior to or during brain deformation, where each 3D point of the first 3D point cloud 415 is color-encoded. The step of obtaining a first 3D point cloud 415 includes the steps of optically scanning an exposed brain surface 405 of the living subject at a time prior to or during brain deformation, capturing surface-reflected light from the brain surface of the living subject, acquiring a first point cloud representation of the geometry of the cortical surface from the captured surface-reflected light, and color-encoding the acquired each point of the first point cloud representation by a direct linear transform representation so as to construct the first 3D point cloud 415. In one embodiment, the step of obtaining a first 3D point cloud 415 is performed with an optical device, for example, a LRS 401, which is capable of obtaining frequency, intensity and geometric data with respect to the cortical surface simultaneously. The data provided by the LRS includes the first 3D point cloud, where each 3D point is color-encoded from a RGB photographic image of the FOV acquired at the time of scanning by a direct linear transform (hereinafter "DLT"). The DLT of the LRS is determined at the factory.

At step 420, a DLT mapping between the first 3D point cloud (a physical space) and the first 2D photographic image (a image space) is calculated from the abundance of data acquired by the LRS so as to generate a first 2D photographic image 417 from the first 3D point cloud 415. Since the LRS is tracked using an OPTOTRAK® 3020 and the DLT is known, any photographic image plane can be reconstructed from the LRS digital image data.

Repeating steps 410 and 420 during or after brain deformation will obtain a second 3D point cloud 435 of the brain (step 430), wherein each 3D point of the second 3D point cloud representation is color-encoded, and generate a second 2D photographic image 437 from the second 3D point cloud 435 (step 440), respectively. In one embodiment, steps 410 and 430 are sequentially performed with a time difference, Δt. That is, the first 2D photographic image 417 acquired in SCAN 1 (step 410) represents an image of the FOV before brain deformation has taken place, and the second 2D photographic image 437 acquired in SCAN 2 (step 430) represents an image of the FOV after brain shift has taken place.

At step 450, the first 2D photographic image 417 and the second 2D photographic image 437 are non-rigidly aligned to generate a non-rigidly registered SCAN 1 photographic image 467. Finally, at step 460, a depth map, δ₁, acquired in SCAN 2 (step 430) is applied to the non-rigidly registered SCAN 1 photographic image 467, so as to provide a measurement of shift from the pre-shift scanning (SCAN 1) to the post-shift scanning (SCAN 2).

Specifically, the step of non-rigidly aligning the first 2D photographic image 417 and the second 2D photographic image 417 includes the steps of transforming the first 2D photographic image 417 and the second 2D photographic image 437 from RGB images into corresponding gray level images, and obtaining a final deformation field that registers gray level images one to the other. In one embodiment, the step of obtaining a deformation field comprises the steps of calculating a deformation field for each of a series of levels, wherein each level is corresponding to a particular combination of scale and resolution for an image, and adding all the deformation fields for all of the series of levels to generate the final deformation field.

In practice, the creation of the similar photographic image plane is not always necessary. This translates to the nonrigid registration algorithm accounting for deformation as well as scanner movement, i.e. the acquisition of a different FOV within the photographic image due to a slight difference in the laser scanner's spatial position is accounted for in the nonrigid registration process.

These and other aspects of the present invention are further described below.

METHODS, IMPLEMENTATIONS AND EXAMPLES OF THE INVENTION

For the purposes of comparison and feasibility, conventional methods of cortical surface registration were also performed. For example, for the approach of Nakajima et al. [33], cortical features such as vessel bifurcations are localized in both MR and scanner image spaces and a rigid PBR is then performed between the two spaces. Another registration framework is based on the ICP, where the registration targets became vessel and sulcal contours visible on the MR image and the laser-scanned cortical surface. This suite of registration approaches provides multiple avenues to pursue for determining an optimal cortical surface alignment under varying surgical conditions.

Without intent to limit the scope of the invention, further exemplary procedures and experimental results of same according to the embodiments of the present invention are given below.

Example 1

Phantom Experiment

Figure 5:
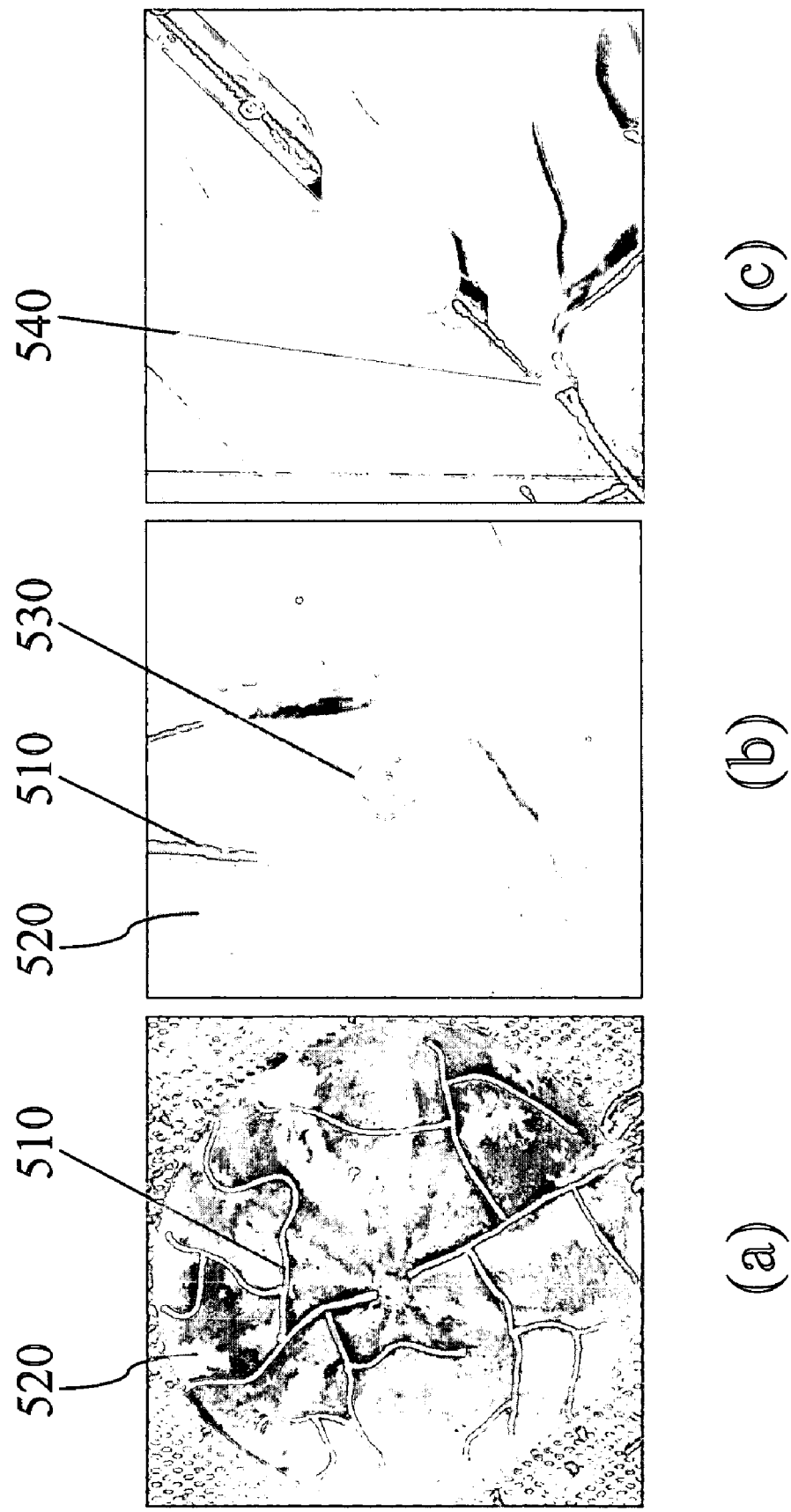
FIG. 5 shows a watermelon phantom used for elaborating accuracy of a cortical surface registration according to one embodiment of the present invention: (a) a watermelon with contrast regent soaked twine laid into carved vessel grooves, (b) the watermelon with a fiducial marker placed at a predetermined position, and (c) the watermelon with an ACUSTAR® divot cap placed at a predetermined position.

To evaluate the accuracy and effectiveness of the SurfaceMI algorithm to register intermodality surfaces, a phantom experiment using a watermelon was conducted. Referring to FIGS. 5a–5c, in the experiment, Omnipaque (Amersham Health PLC, Buckinghamshire, the United Kingdom) soaked twine 510 was laid into the watermelon surface 520 to simulate the appearance of contrast-enhanced vasculature on the brain surface in CT, and/or MR imaging. Rigid fiducial markers 530, such as ACUSTAR® (Z-Kat, Inc., Hollywood, Fla.), were implanted into the watermelon surface 520 for alignment of one image space to another one. The ACUSTAR® fiducial markers 530 were filled with CT and/or MR visible contrast enhancement liquid. In addition, ACUSTAR® divot caps 540 were placed at soaked twine (vessel) bifurcations for target localization. The phantom was imaged by a CT imager, such as Mx8000, (Philips Medical Systems, Bothell, Wash.), and scanned by a LRS, e.g., RealScan3D, and digitized by a spatial tracking system such as OPTOTRAK® 3020, respectively. Therefore, the phantom was represented by three coordinate systems including a CT image coordinate system, an OPTOTRAK® coordinate system, and a LRS coordinate system. Other fiducial markers, CT imagers, LRS and spatial tracking systems can also be used to practice the current invention.

Figure 6:
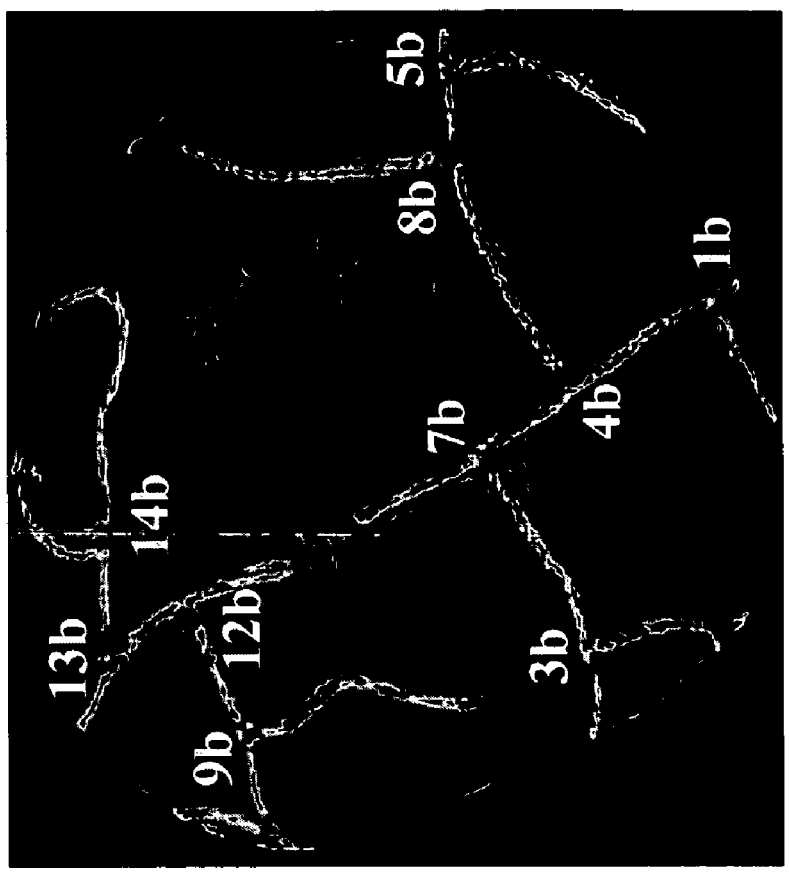
FIG. 6 shows volume rendering of image data having fudicial makers and localized target points: (a) fudicial markers A–F and manually localized landmarks 1–15 in the image space and OPTOTRAK® coordinate systems, and (b) landmarks localized in LRS coordinate system.
Figure 6:
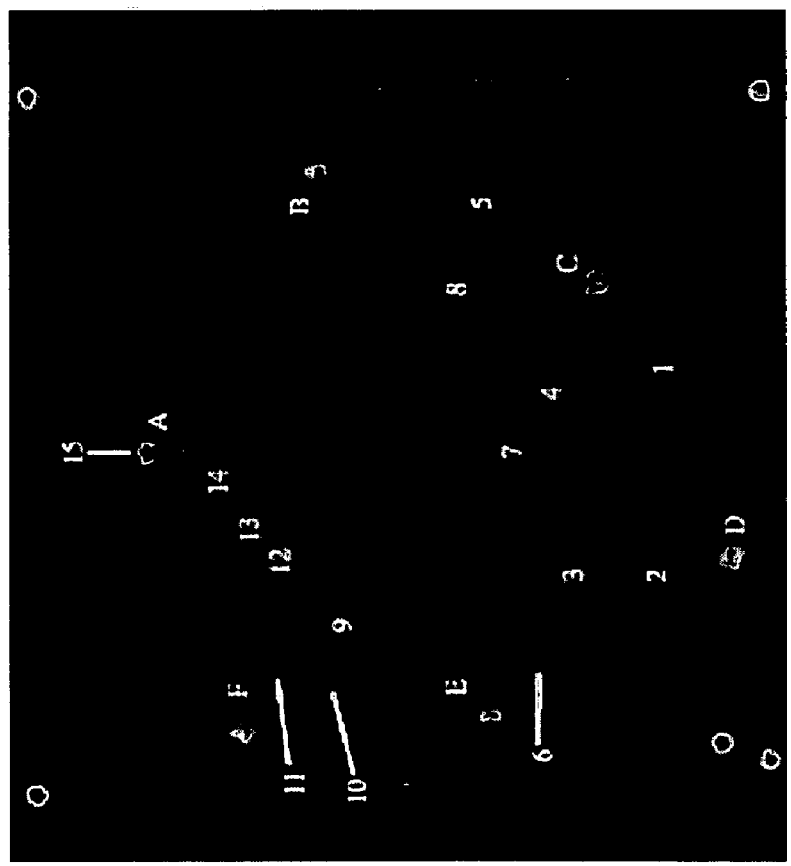

It is crucial to accurately to localize targets of interest during surgery for the IGS. For comparison, various registrations were performed, and fiducial registration errors (hereinafter "FRE") and target registration errors (hereinafter "TRE"), as defined by Mandava and Fitzpatrick [36, 37], were examined. The first registration aligned the CT image space coordinate system, img, to the OPTOTRAK® coordinate system, opto, using the ACUSTAR® fiducial markers in each modality. The alignment is to find a transformation from the image space coordinate system to the OPTOTRAK® coordinate system, $T_{img \to opto}$. FRE and TRE were calculated for the registration so as to provide an optimal registration of a physical space to an image space. FIG. 6a shows the locations of the six fiducial markers A–F and fifteen manually identified target points 1–15 in a volume rendering of an image of the watermelon phantom.

Having established this registration optimum, corresponding sets of manually identified points at vessel bifurcations in img and opto were registered to provide quantitative validation of Nakajima's method of using cortical features for registering the physical space to the image space. Additionally, ten visible bifurcation points 1b, 3b, 4b, 5b, 7b–9b, and 12b–14b in a LRS space, lrs, were localized, as shown in FIG. 6b. These points respectively correspond to manually identified points 1, 3, 4, 5, 7–9, and 12–14 in img and opto, as shown in FIG. 6a, and used for the PBR registration as a verification of Nakajima's method applied to the LRS data. FRE was calculated for all registrations, i.e., $T_{img \to opto}$, $T_{img \to lrs}$, and $T_{opto \to lrs}$. The manually identified target points in each space were localized three times and averaged to minimize localization error.

The other methods for intra-operative registration were also examined within the context of the phantom experiment. The ICP registration was performed using phantom vessel contours extracted using simple threshold from the LRS and CT data. The SurfaceMI framework was used to align the segmented surface. For each registration, a reduced region of the watermelon LRS surface was extracted to simulate the approximate size of the surgical FOV. For both registration methods of the ICP and SurfaceMI, an initial alignment of the surfaces was provided by using three manually localized targets visible in the segmented surface. TRE was calculated in both registration frameworks using seven novel surface targets (i.e., those landmarks that were not in the surgical FOV) and was compared to the TRE provided by the PBR alignment of vessel landmarks.

Robustness studies for the registration frameworks were carried out by perturbing initial landmarks uniformly along the surface of a sphere fitted to the target point cloud, i.e., perturbing the landmarks in spherical coordinates ϕ, θ and Φ at the fitted radius r. The perturbations were independently and uniformly sampled from −2.5° to 2.5° (simulates approximately 1 cm fiducial localization error, i.e., perturbation arc length $r_\ominus$=9.29 mm) in each spherical axis for each trial, and each framework was subject to 500 perturbation trials. The results of this experiment provide insight as to the efficacy of the registration frameworks given suboptimal initial conditions.

Figure 7:
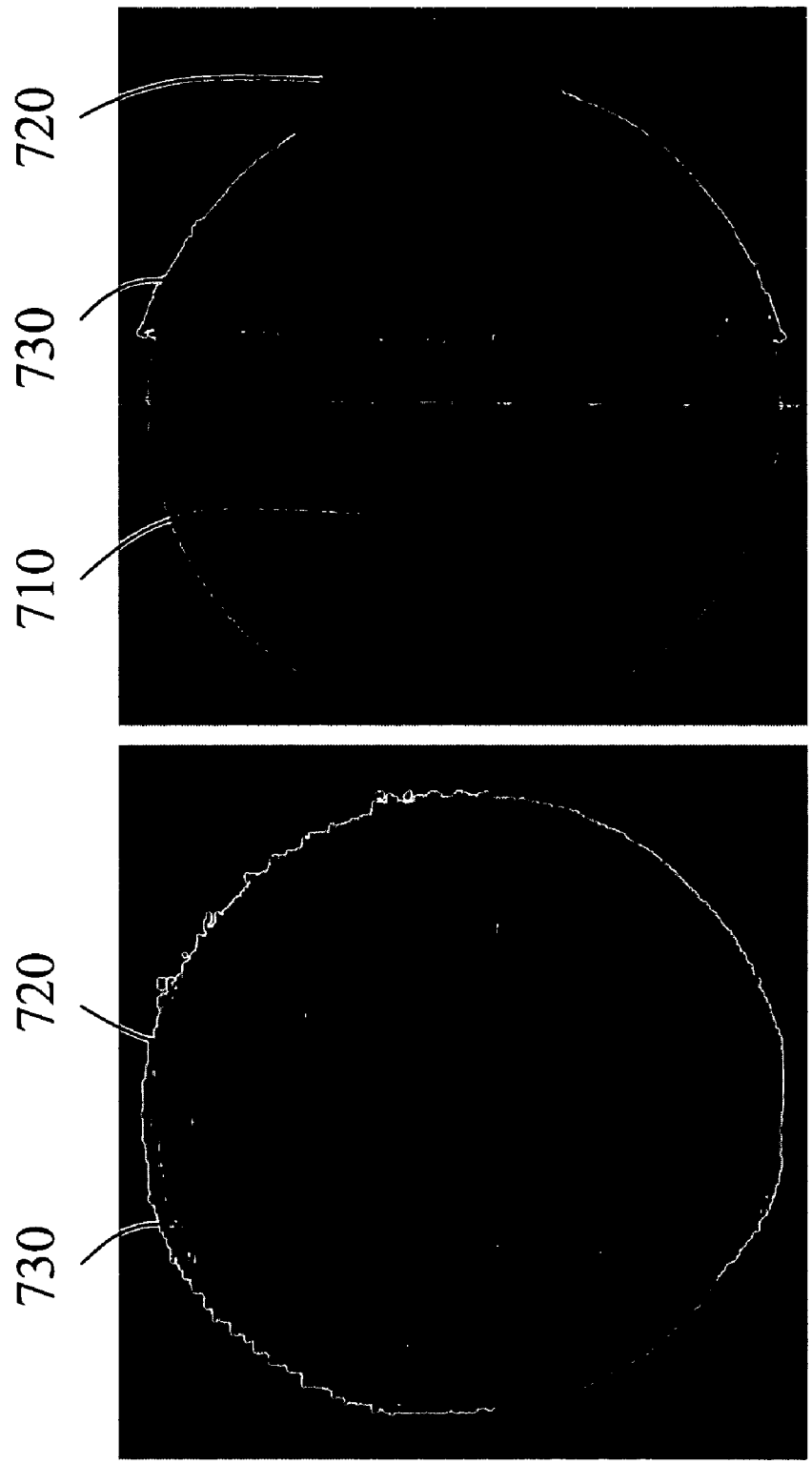
FIG. 7 shows a simulated deep tissue sampling according to one embodiment of the present invention: (a) a front view of the deep tissue sampling region, and (b) a side view of the deep tissue sampling region.

Accuracy of the registration frameworks with regard to deep tissue targets was also investigated. For this experiment, deep tissue targets were sampled in a 5 cm radius of the centroid of the manually localized surface points. The sampling was constrained to only deep tissue targets, i.e., sample points which lie in both the sphere and watermelon, as shown in FIG. 7. The larger sphere 710 demonstrates the geometric sphere fit of the point cloud 730. The smaller sphere 720 represents a sampling region with radius of 5 cm, centered about the centroid of the localized fiducials. The volume of overlap demonstrates the deep tissue sampling region. True positions of the deep tissue targets were found in LRS space by transforming targets from image space using the rigid-body transformation $T_{img \to lrs}$ (based on identifying vessel points in both modalities). These same tissue targets in image space were also registered to LRS using transformations based on SurfaceMI which when compared served as an estimate of TRE.

The registration results achieved with implantable markers were comparable to previously published data [1]. ACUSTAR® fiducial marker system, the mean FRE of 0.3±0.1 mm was achieved using six markers. The mean TRE for this registration was 1.7±0.3 mm using fifteen target landmarks. These results demonstrate the accuracy associated with implantable fiducial markers and provide a baseline for comparison with subsequent registrations.

TABLE 1

TRE for the three registration methods, PBR, ICP, and SurfaceMI, in the watermelon phantom experiment on a LRS surface that approximates a surgical FOV. Three landmarks were used as fiducials and seven targets were used to calculate TRE.

| Registration Method | Mean TRE (mm) |
|---|---|
| PBR | 2.6 ± 0.7 |
| ICP | 2.4 ± 0.8 |
| SurfaceMI | 2.5 ± 0.7 |

The registration results for the phantom experiment concerned with the alignment of the cortical surface using vessel-based landmarks show excellent correlation with the previously published studies of Nakajima et al. [33]. FRE for ten manually localized landmarks in all three spaces, i.e., opto, img, and lrs, was 1.3±0.5 mm and 1.7±0.6 mm for $T_{img \to opto}$ and $T_{img \to lrs}$, respectively. In addition, a second PBR was calculated using a subset of the vessel markers in a focal cortical region to simulate vessel fiducials within a craniotomy. The remaining vessel bifurcations outside the simulated surgical FOV were used as targets. The TRE is listed in Table 1.

As an aside, a measurement of localization precision was calculated since each set of landmarks (i.e., in img, opto, and lrs) was identified three times. Precision was measured as the mean standard deviation for each measurement (x, y, z) in corresponding landmarks across the three trials. For the landmarks selected in img, the mean standard deviations in x, y, and z were 0.27, 0.28, and 0.31 mm, respectively. In opto, the mean standard deviation in x, y, and z are 0.35, 0.22, and 0.13 mm, respectively. For the ten landmarks chosen in lrs, the mean standard deviations in x, y, and z were 0.71, 0.58, and 1.14 mm.

Figure 8:
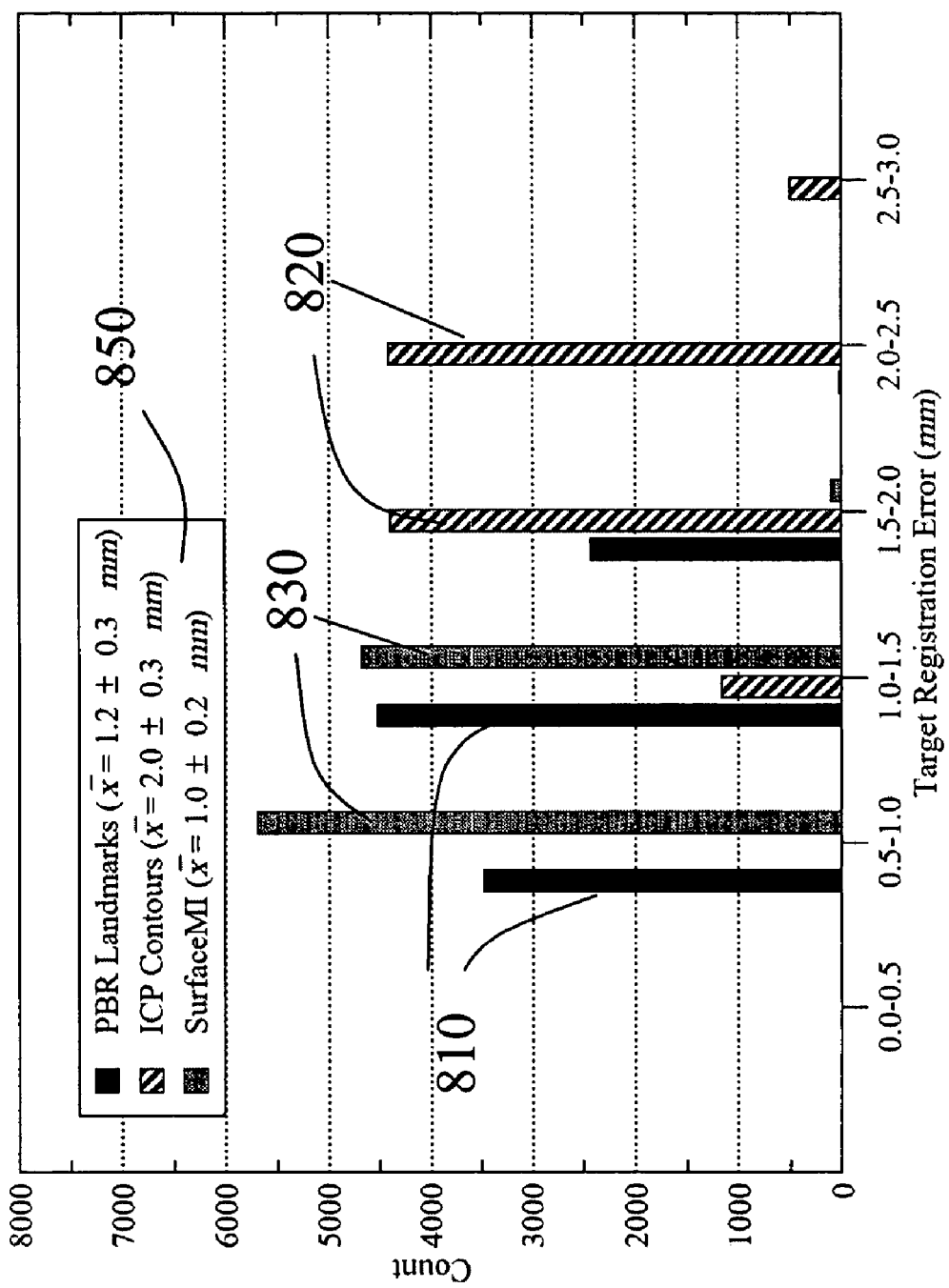
FIG. 8 shows a TRE histogram for deep tissue targets using PBR on surface landmarks, ICP registration on surface contours, and SurfaceMI on textured surfaces, respectively, according to one embodiment of the present invention.
Figure 9:
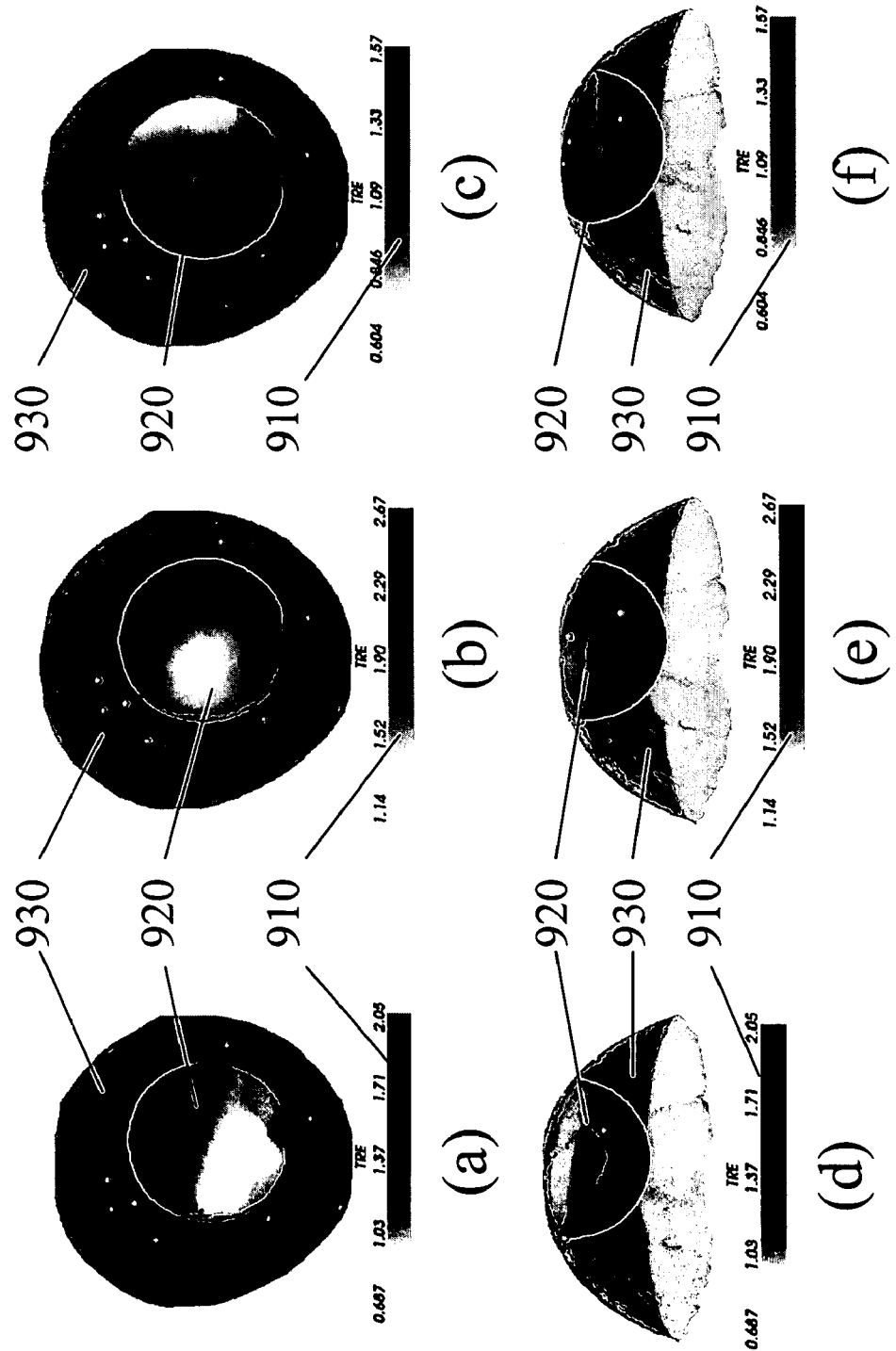
FIG. 9 shows a 3D distribution of the TRE for deep tissue targets as shown in FIG. 8: (a), (b), and (c) a top view of the watermelon surface with the TRE distribution using PBR, ICP, and SurfaceMI, respectively, (d), (e), and (f) a front view of the watermelon surface with the TRE distribution using PBR, ICP, and SurfaceMI, respectively.

Referring now to FIGS. 8–11 and first to FIG. 8, a histogram and mean TRE for simulated deep tissue targets is shown. Bars 810, 820 and 830 shown in FIG. 8 represent the TRE histogram for deep tissue targets using the PBR-based registration on surface landmarks, the ICP-based registration on surface contours, and the SurfaceMI on textured surfaces, respectively. Corresponding mean TRE 850 of the deep tissue targets using the PBR-based registration on surface landmarks, the ICP-based registration on surface contours, and the SurfaceMI on textured surfaces are 1.2±0.3 mm, 2.0±0.3 mm, 1.0±0.2 mm, respectively. FIG. 9 shows a 3D distribution 930 of the TRE for the deep tissue targets shown in FIG. 8 overlaying the watermelon image volume 920. FIGS. 9a, 9b and 9c are a top view of the 3D TRE distribution 920 for the deep tissue targets using the PBR-based registration on surface landmarks, the ICP-based registration on surface contours, and the SurfaceMI on textured surfaces, respectively, while FIGS. 9d, 9e and 9f are a side view of the 3D TRE distribution 920 corresponding to FIGS. 9a, 9b and 9c, respectively. Each deep tissue sample of the TRE distribution 920 is grayscale encoded on the watermelon s image volume 930 with the range of scalar values of the TRE being shown in a bar 910 associated with each figure. The results shown in FIGS. 8 and 9 suggest that SurfaceMI predicts the deep tissue targets more accurately then the PBR and ICP registration methods.

Figure 10:
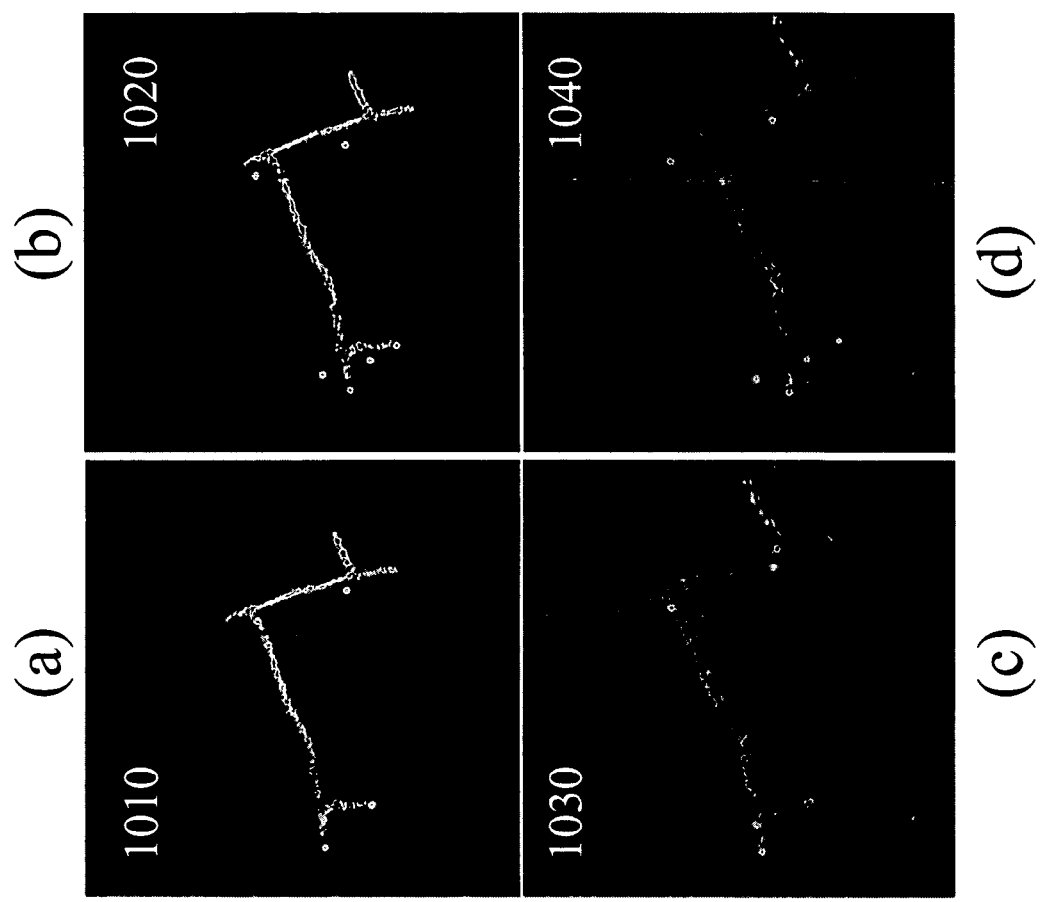
FIG. 10 shows intermodality registration results of two textured surfaces using ICP and SurfaceMI, respectively, according to one embodiment of the present invention: (a) ICP registration with a given initial landmark perturbation, (b) ICP registered, (c) SurfaceMI registration with a given initial landmark perturbation, and (d) SurfaceMI registered.
Figure 11:
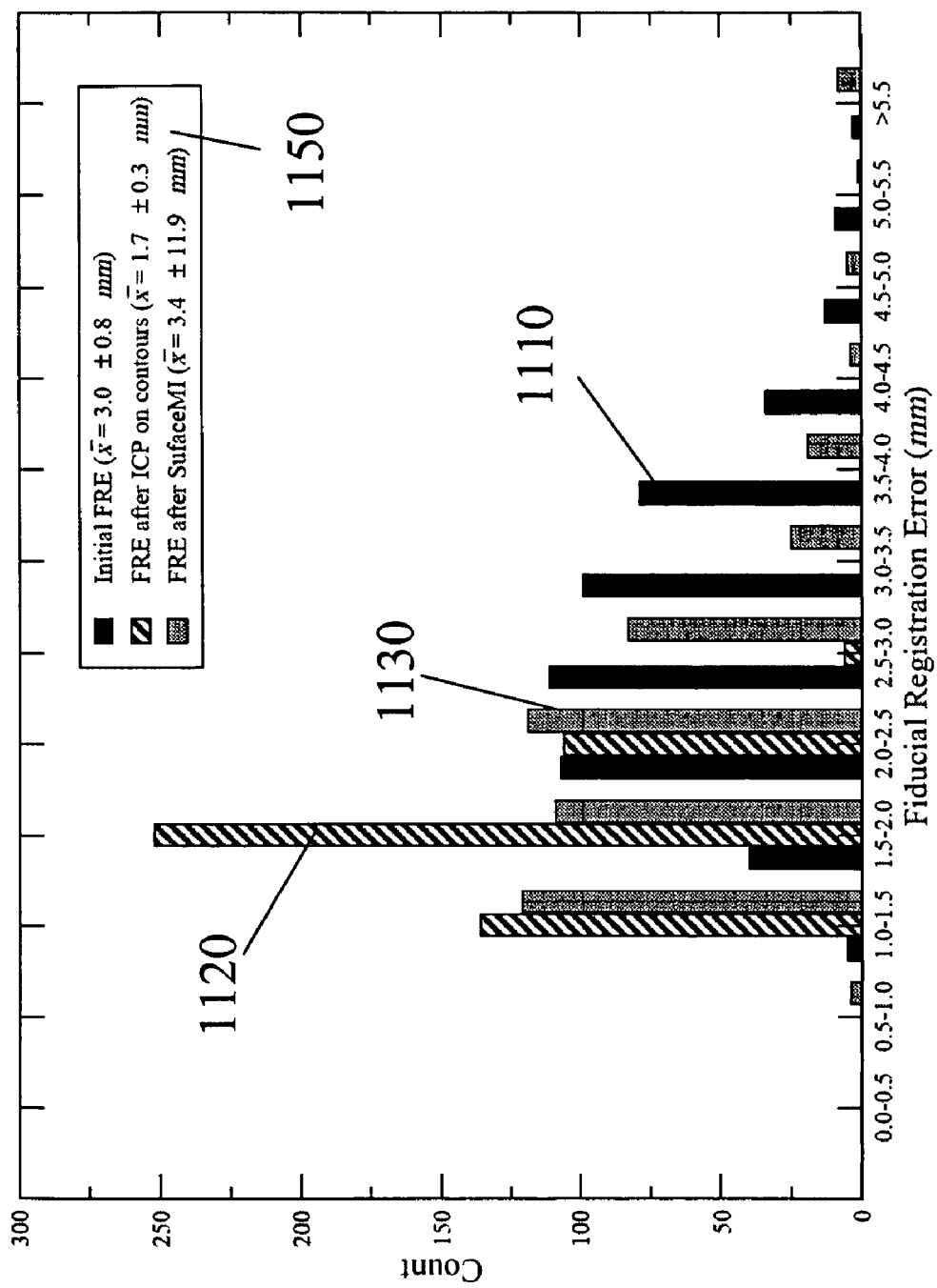
FIG. 11 shows a FRE histogram with a given initial landmark perturbation according to one embodiment of the present invention. The landmarks in the FOV were perturbed up to ±2.5° in each spherical coordinate ($\phi$, $\Phi$, $\theta$) in an image space.

In addition to reporting registration results based on a routine application of each alignment framework, a series of robustness studies was performed to investigate the effects of varied initial guesses (i.e., an approximate 1 to 6 mm fiducial localization error with individual fiducial error as large as 9.3 mm). Examples of the registration provided by the ICP and the SurfaceMI with a given initial landmark perturbation are shown in FIG. 10. The ICP registration with a perturbed initial condition 1010 and the ICP registered condition 1020 is shown in FIGS. 10a and 10b, respectively, while a SurfaceMI registration with a perturbed initial condition 1030 and a SurfaceMI registered condition 1040 are shown in FIGS. 10c and 10d, respectively. It should be noted that there is a texture projected on the surface of the watermelon that is an artifact of the rendering process, i.e., this texture did not affect the registration process. A gross-scale representation of the texture, which is a result of the slice-to-slice spacing in the CT image, can be seen in FIG. 6a for comparison. FRE results from these perturbation studies using the PBR, the ICP, and the SurfaceMI registrations on the same cortical sub-region used for the TRE studies of Table 1 are shown in FIG. 11 over 500 trials. The landmarks in the FOV were perturbed up to ±2.5° in each spherical coordinate ($\phi$, $\Phi$, $\theta$) in the image space. In FIG. 11, bars 1110, 1120 and 1130 represent a histogram of the FRE using the PBR, the ICP, and the SurfaceMI registrations, respectively. Corresponding mean FRE 1150 using the PBR, the ICP, and the SurfaceMI registrations are 3.0±0.8 mm, 1.7±0.3 mm, 3.4±11.9 mm, respectively. As shown in FIG. 11, the distribution of the FRE ranges from 1.0 to 5.8 mm for the three landmarks used in an initialization of the ICP and SurfaceMI registrations. For the ICP registration on the surface contours, the FRE is reduced by approximately 43%. While the SurfaceMI registration produces some outliers. Using the extreme studentized deviate (hereinafter "ESD") [38], eight outliers were detected with >99.95% confidence. Removing these outliers from the SurfaceMI trials produced a mean FRE of 2.2±0.8 mm, reducing FRE by approximately 27%.

In a summary, initial studies using rigid markers were performed to provide baseline registration accuracy with respect to unknown errors associated with the phantom and/or imaging method; results reflected comparable accuracies reported in the literature [1]. The next set of studies used vessel bifurcations localized in all modalities as the basis for registration. Reassuringly, the FRE between img and opto using the manually localized vessel bifurcations were comparable to values reported by Nakajima et al. Similar values were also determined when registering vessel bifurcations using LRS data within the context of PBR, ICP, and SurfaceMI. This would indicate that using techniques similar to Nakajima et al. should be achievable using LRS data. In addition to reporting error within the simulated craniotomy region, targets outside the focal region were also used to assess alignment quality. Overall, the difference between results among all three methods was negligible. The increased magnitude of TRE over FRE agrees with an accepted understanding regarding the effects of fiducial placement on target registration error; that is, even with a low FRE, a sparse number of fiducials localized within a concentrated area can precipitate a "lever-arm" effect in areas remote to the registration region. Interestingly, a different result is seen with respect to targets in close proximity to the subregion of interest on the watermelon surface. FIG. 8 reports the distribution of TRE data compared among all three registration approaches. With respect to the mean TRE error for the entire region, SurfaceMI performed the best with an average TRE of 1.0 mm. When comparing deep tissue results between the PBR and SurfaceMI methods, as shown in FIG. 9, PBR has a greater range of TRE error than SurfaceMI, which may be due to the difficulty in localizing bifurcations upon the LRS data for PBR methods. The ICP registration performed considerably worse, and this may be due to the contour threshold process. More specifically, any spatial noise contained within the thresholded vessel structure is not averaged out as well within the ICP framework when compared to using a denser point cloud. This possible source of error would not be present within the SurfaceMI approach since the dense geometric data are maintained and the fine adjustments to alignment are provided by an intensity-based registration. SurfaceMI and PBR produced comparable results although the TRE spatial distribution for deep tissue targets was greater for the PBR method. This may suggest that the effects of a combined surface and intensity approach produce a lower error due to the averaging effects associated with the registration metrics used in SurfaceMI. When comparing SurfaceMI to ICP, the results suggest that vessel contours alone may not be the best approach to cortical surface registration, but rather, the addition of the intensity data provides significant refinement to the alignment.

Example 2

Clinical Trials

For clinical data acquisitions, the LRS approved by the VUIRB uses a Class I "eye-safe" laser and is mounted on a vibration damping monopod. Immediately after duratomy, the LRS is brought into the surgical FOV and the scanning extents (left and right scanning margins) are set to cover the width of the craniotomy. A laser stripe is then passed over the FOV and sampled 500 times between extents. Each sampling of the line produces 256 3D sample points, which results a practical point cloud density of approximately 100,000 points per scan. Immediately following the range scan, an RGB-bitmap (texture) of the scanning FOV is acquired and texture map coordinates are assigned to each 3D point via manufacturer calibration. Data acquisition by the LRS takes on the order of 15 to 30 seconds, with approximately 1.5 minutes of intra-operative time spent per scan (i.e. bring the LRS into the surgical FOV, calibrate extents and acquire, then remove from the FOV). Clinical data acquisitions for three patients are highlighted as follows.

Figure 12:
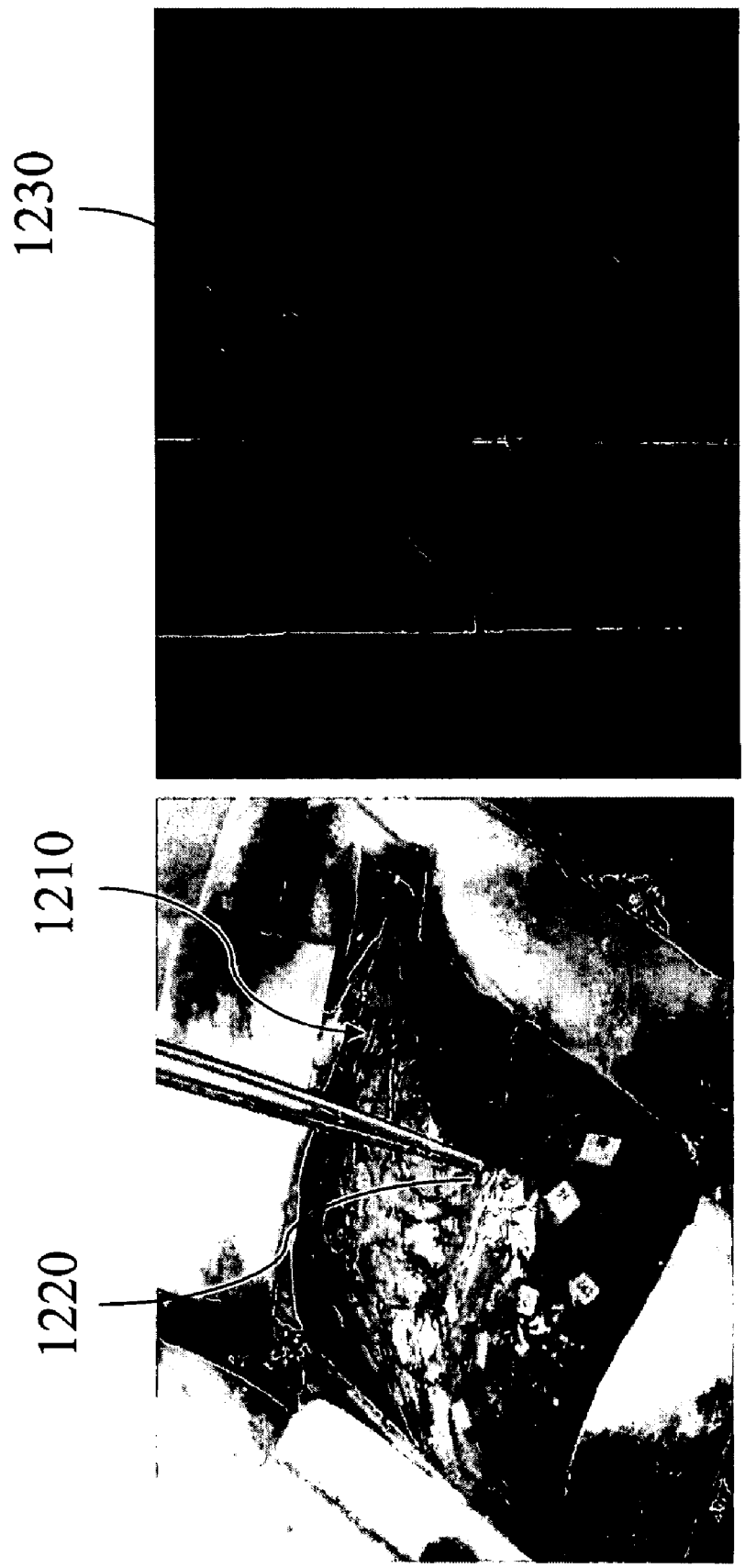
FIG. 12 shows an intra-operative LRS data acquired from a first patient according to one embodiment of the present invention: (a) digital photographic image with the vein of Trolard highlighted, and (b) a textured point cloud generated intra-operatively by a LRS.

The first patient was a 37-year old man with a six-week history of focal motor seizures. MR imaging revealed a hypointense nonenhancing mass in the posterior, superior left frontal lobe, abutting the motor strip. An awake resection was operated for the patient, with motor and speech mapping. Intra-operatively, he was placed in the supine position, with the vertex of the head elevated 15° and the head turned 30° to the right. A fronto-temporal-parietal craniotomy was performed and the tumor was localized using ultrasound and frameless stereotaxy. The vein of Trolard coursed superiorly to the superior sagittal sinus, immediately behind the posterior extent of the tumor and directly in front of the motor gyrus. After mapping of the speech and motor regions of the face and arm, gross total resection of the tumor was accomplished. The patient tolerated the procedure without neurological sequelae. Intra-operatively, following durotomy, the LRS such as RealScan3D was moved into position via the customized monopod above the craniotomy site at approximately 30 to 45 cm from the brain's surface. The LRS was activated and acquired approximately 20,000 points in 5 to 7 s. Following retrieval of the LRS data, registration between the patient's intra-operative LRS data and a pre-operative MR image volume were performed retrospectively. Referring to FIG. 12, a digital photograph image 1210 of the surgical FOV with the vein of Trolard 1220 highlighted, a corresponding textured point cloud 1230 generated intra-operatively using the LRS are respectively shown in FIGS. 12a and 12b.

Figure 13:
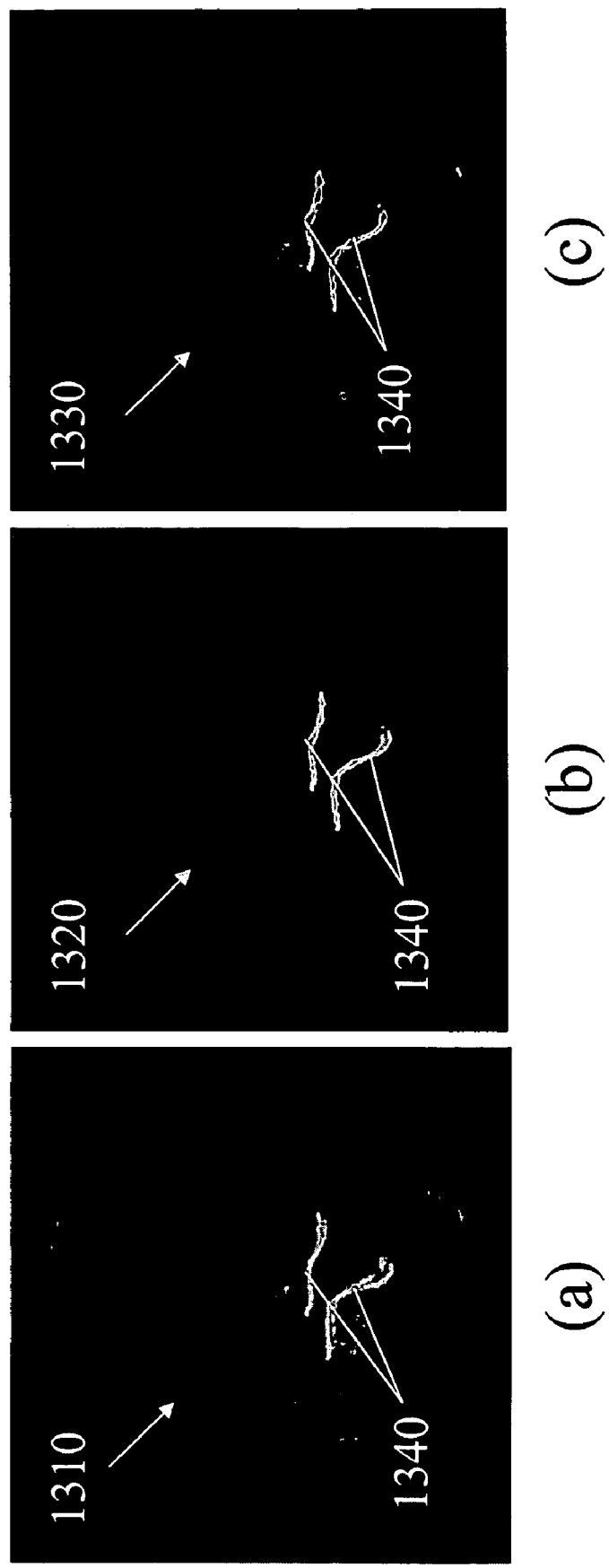
FIG. 13 shows registration results from intra-operative data according to one embodiment of the present invention: (a) PBR using manually localized landmarks in an image space and a LRS space, (b) ICP registration using highlighted contours in the image space and the LRS space, and (c) SurfaceMI registration given the initial alignment provided by the PBR method. The highlighted contours are prominent sulcal and vessel patterns visible in both spaces.

Central to using the LRS within the clinic is to demonstrate in vivo registration results. A clinical example of registration results from intra-operative data is shown in FIG. 13 with corresponding measures of registration error listed in Table 2. Specifically, FIG. 13a shows the result 1310 of PBR-based registration using manually localized landmarks in img and lrs. FIG. 13b shows the result 1320 of the ICP registration using highlighted contours 1340 in img and lrs. And FIG. 13b shows the result 1330 of the SurfaceMI registration given the initial alignment provided by the PBR method. The highlighted contours 1340 are prominent sulcal and vessel patterns visible in both img and lrs spaces. For Table 2, the first, second and third columns represent the registration methods used, the mean registration error associated with the cortical surface points used in PBR, and the mean closest point residual between contours, respectively. Although PBR registration results in better fiducial error than the ICP and SurfaceMI registrations, as shown in Table 2, the results shown in FIG. 13 suggest that the registration error reported for the contour points (ICP and SurfaceMI registrations) is the better metric as to the quality of alignment than the PBR registration.

TABLE 2

Registration errors for in vivo alignment using PBR, ICP, and SurfaceMI frameworks.

| Registration Method | Mean Error Measure (mm) Fiducial Points (n = 3) | Mean Error Measure (mm) Contour Points (n = 468) |
|---|---|---|
| PBR | 2.4 ± 1.0 | 1.9 ± 1.0 |
| ICP | 3.4 ± 1.4 | 0.9 ± 0.6 |
| SurfaceMI | 3.5 ± 1.7 | 1.3 ± 0.5 |

The results from the clinical experiment of the first patient demonstrate the feasibility of cortical surface registration in the OR environment as well as provide a limited quantitative assessment to the approach's accuracy. Table 2 demonstrates that a PBR approach similar to Nakajima et al. (except using LRS data in lieu of optical digitization) produces a mean registration error for vessel fiducials that is 1-mm less on average than that provided by ICP or SurfaceMI. However, in the region of the contours, the method did not fare as well. FIG. 13 demonstrates a qualitatively better alignment in the area of the contours when using either ICP or SurfaceMI. Table 2 also quantifies this improved closest point residual for ICP and SurfaceMI over the PBR method. One likely reason for this discrepancy is that brain deformation may have occurred upon opening the cranium and may be distributed nonuniformly over the brain surface. This would be consistent with the results in Table 2 since the PBR method relies on the selection of the vessel fiducials as the basis for registration while ICP and SurfaceMI only use these for initialization. Hence, if the brain surface is non-uniformly deformed, it would logically follow that methods which base their registration on the vessel fiducials (PBR) would be better within the fiducial region, while methods that use contour information (SurfaceMI and ICP) would be better within the contour region.

The clinical results of the first patient also demonstrate that the registration protocol used within this work may be a viable approach for surgeries where minimal brain shift is encountered. In addition, the visual results shown in FIG. 13 provide new anatomical cues to surgeons by correlating the FOV observed in the OR to the MR tomogram volume studied prior to surgery for pre-operative planning.

The second patient was a 34-year old man with a two-year history of paroxysmal headaches in the bitrmporal regions and a more recent history of emotional liability. He was otherwise asymptomatic and his past medical history was unremarkable. Neurological examination was normal. MR imaging was performed to evaluate persistent headaches and revealed a left inferior frontal region tumor, which measured 2.5×2.0 cm. There was some calcification within the tumor, but little enhancement with gadolinium infusion; these findings were most consistent with a low-grade glial neoplasm. Because of the proximity of the lesion to the speck cortex, an awake craniotomy, with cortical mapping, was performed, complemented by frameless stereotactic guidance. The patient was placed supine on the operating table and the head was elevated 10° and turned 60° toward the right. A left fronto-temporo-parietal craniotomy was performed and the dura opened in a cruciate fashion to expose the frontal, anterior temporal and enterior parietal lobes as well as the sylvian fissure and vessels. In the anterior inferior left frontal region, an enlarged and discolored gyrus was identified and was felt to be the tumor by visual inspection as well as by altrasound examination and frameless stereotactic location. Mapping of Broca's ares was performed and demonstrated that the speech area was separated from the tumor by one gyrus. Gross total resection of the tumor was performed. Post-operatively, he was neurologically intact.

Figure 14:
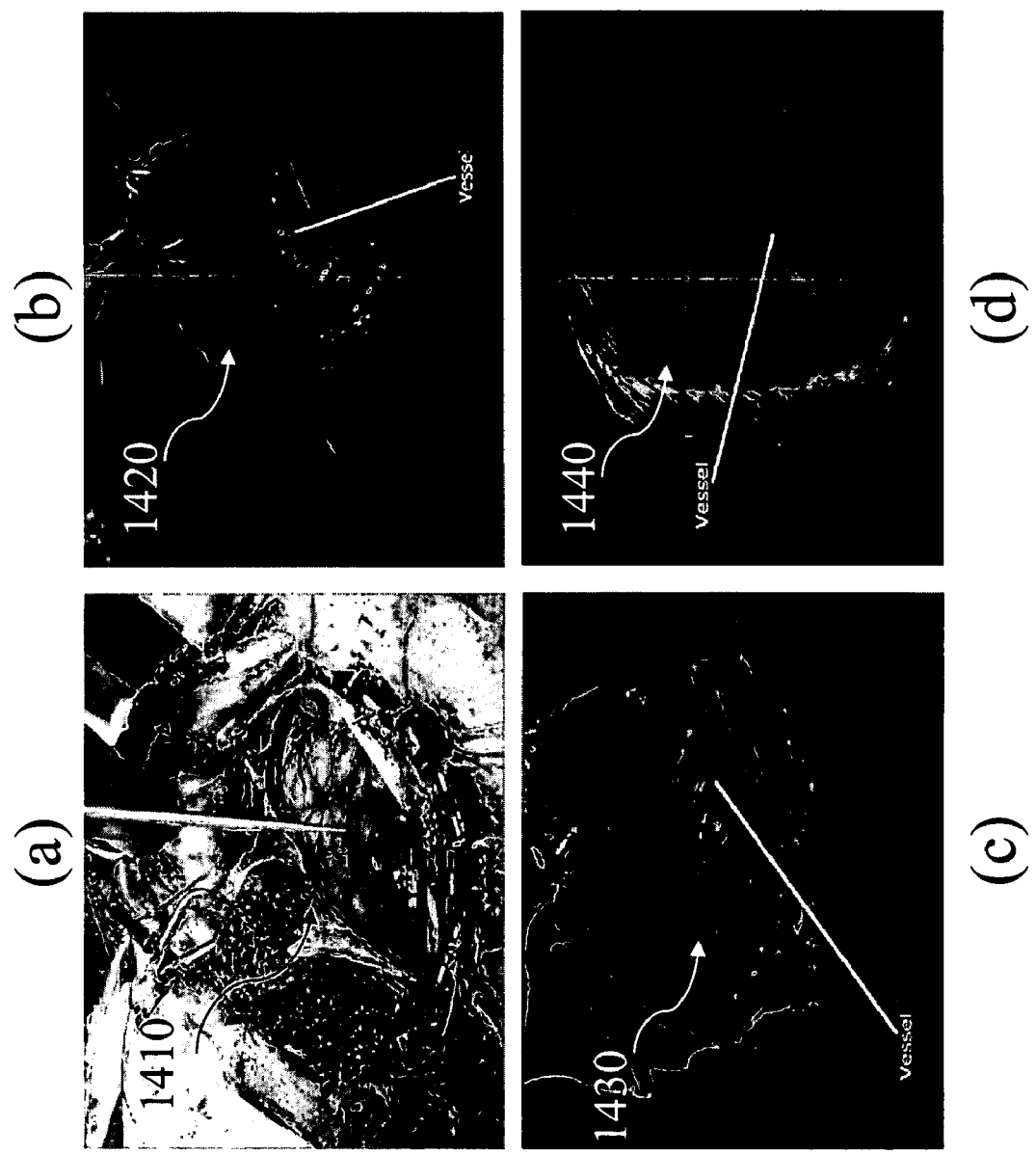
FIG. 14 shows an intra-operative LRS data and pre-operative data acquired from a second patient, respectively: (a) digital photographic image of the scanning FOV, (b) texture image captured at the time of range scanning, (c) texture point cloud of the intra-operative surgical FOV generated via range scanning and texture mapping, and (d) textured point cloud generated from the pre-operative image via ray casting.

Referring now to FIG. 14, the results of data acquisition for the patients include a digital image 1410 of the scanning FOV, a texture image 1420 captured at the time of range scanning, a texture point cloud 1430 of the intra-operative surgical FOV generated via range scanning and texture mapping, and a textured point cloud 1440 from the pre-operative image generated via ray casting. For the patient, the original LRS point cloud consisted of 96,407 points. Segmentation of the cortical surface from the original cloud resulted in a point cloud density of 13,429 points. The physical dimensions of the segmented cloud spanned a surface area of 31.6 cm$^2$, and were recorded at a mean distance of 26.6 cm from the origin of the scanners coordinate system. Table 3 lists the mean TRE using the PBG, ICP and SurfaceMI registrations, respectively, for the second patient. Comparing to the PBR and ICP registrations, the SurfaceMI registration results in a more accurate registration (1.95 mm MRE).

TABLE 3

Mean TRE for the second patient.

| Registration Methods | Mean TRE (mm) |
|---|---|
| PBR | 2.86 |
| ICP | 3.18 |
| SurfaceMI | 1.95 |

Figure 15:
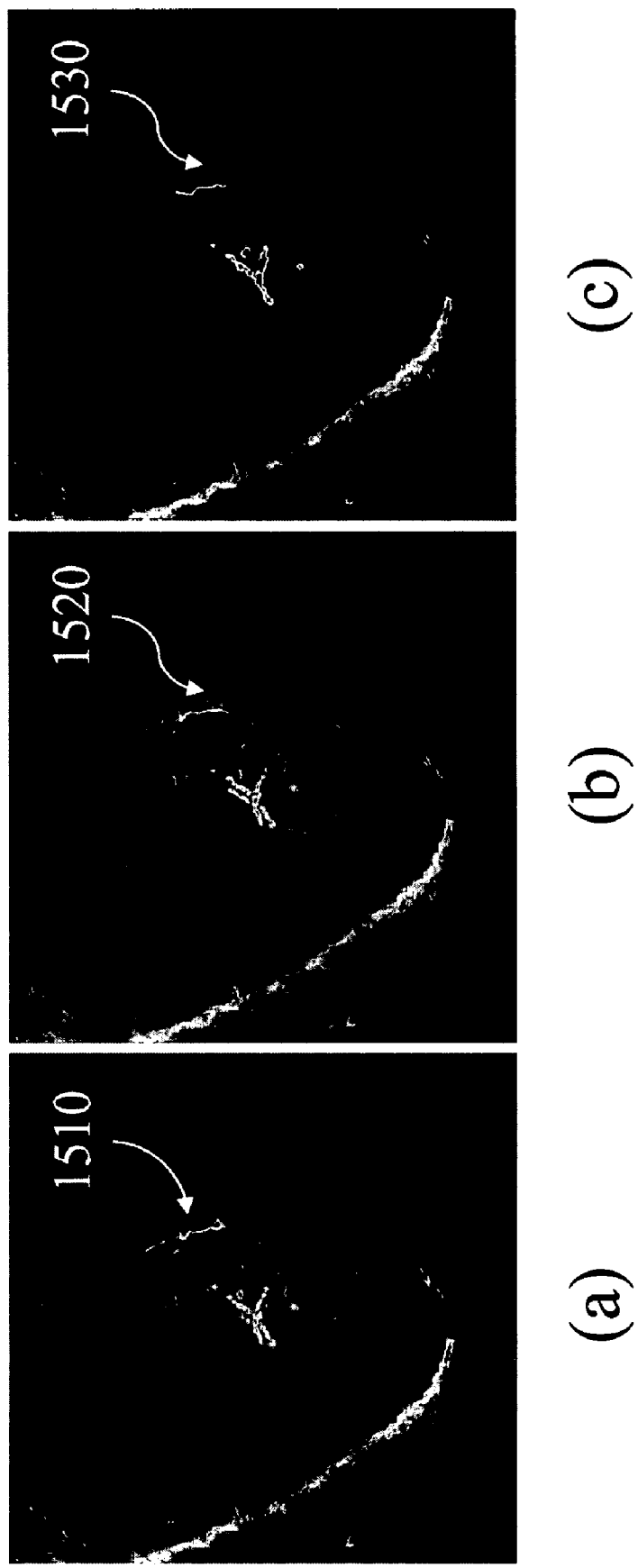
FIG. 15 shows registration results using the data of FIG. 14: (a) using cortical surface landmarkers and PBG, (b) using ICP transforms on the two surfaces, and (c) SurfaceMI registration. The LRS point cloud has been artificially textured to enhance contrast.

Registration results of different methods for the data of FIG. 14 are shown in FIG. 15, where the registration result 1510 is generated by the cortical surface landmarkers and PBG, the registration result 1520 is generated by the ICP transforms on the two surfaces, and the registration result 1530 is generated by the SurfaceMI registration. The LRS point cloud has been artificially texture to enhance contrast. As shown in FIG. 15, the SurfaceMI produces a better registration result than the PBR and ICP method for the patient.

The third patient was a 47-year old woman with breast cancer who had undergone modified radical mastectomy, radiation, and chemotherapy two years prior to her presentation with left arm pain and numbness and subjective left arm and leg weakness. MR demonstrated a 2.5×2.5 cm right posterior frontal mass with significant edema and mass effect, suggestive of metastatic cancer. An awake craniotomy was conducted for the patient with frameless stereotaxy and cortical mapping. The patient was posterior supine, with the head elevated 5 to 10 and turned 15° to 20° to left. A frontal-parietal craniotomy was performed, exposing the midline and the vein of Trolard. The tumor was located in the posterior right frontal region, one gyrus in front of the motor strip. Gross total resection of a metastatic breast carcinoma was performed. Post-operatively, the patient was neurologically intact.

Figure 16:
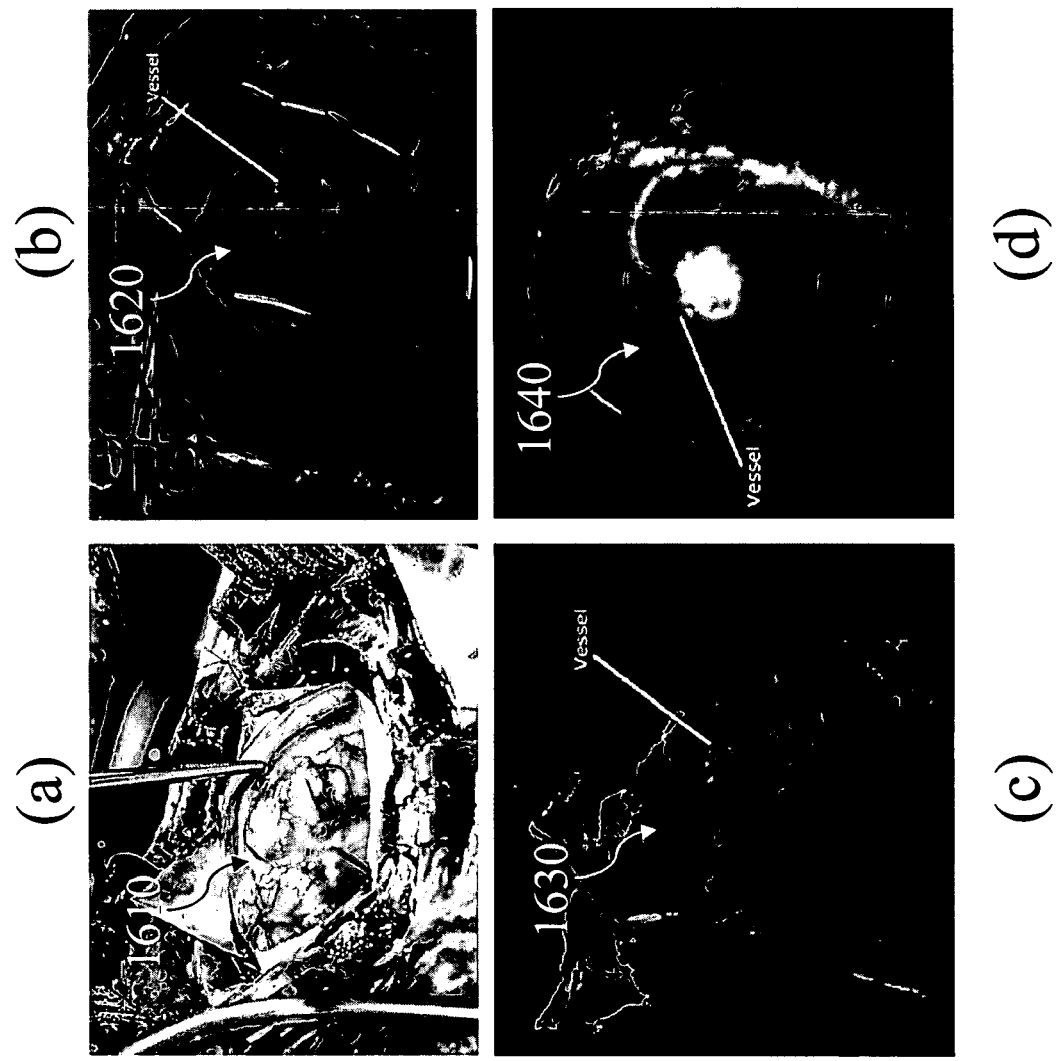
FIG. 16 shows an intra-operative LRS data and pre-operative data acquired from a third patient, respectively: (a) digital photographic image of the scanning FOV, (b) texture image captured at the time of range scanning, (c) texture point cloud of the intra-operative surgical FOV generated via range scanning and texture mapping, and (d) textured point cloud generated from the pre-operative image via ray casting.

Referring now to FIG. 16, the results of data acquisition for the third patients include a digital image 1610 of the scanning FOV, a texture image 1620 captured at the time of range scanning, a texture point cloud 1630 of the intra-operative surgical FOV generated via range scanning and texture mapping, and a textured point cloud 1640 from the pre-operative image generated via ray casting. For this patient, the original cloud contained 96,345 points and the segmented cloud contained 11,688. The physical dimensions of the segmented cloud spanned a surface area of 22.3 cm$^2$, and were recorded at a mean distance of 25.7 cm. The standard deviation in the depth measurement for patient 1 was 4.3 mm and 3.4 mm for patient 2. Table 4 lists the mean TRE using the PBG, ICP and SurfaceMI registrations, respectively, for the third patient. In this clinical trial, the SurfaceMI registration results in a less accurate registration (6.11 mm MRE), comparing to the PBR and ICP registrations.

TABLE 4

Mean TRE for the third patient

| Registration Methods | Mean TRE (mm) |
| --- | --- |
| PBR | 2.55 |
| ICP | 1.91 |
| SurfaceMI | 6.11 |

Figure 17:
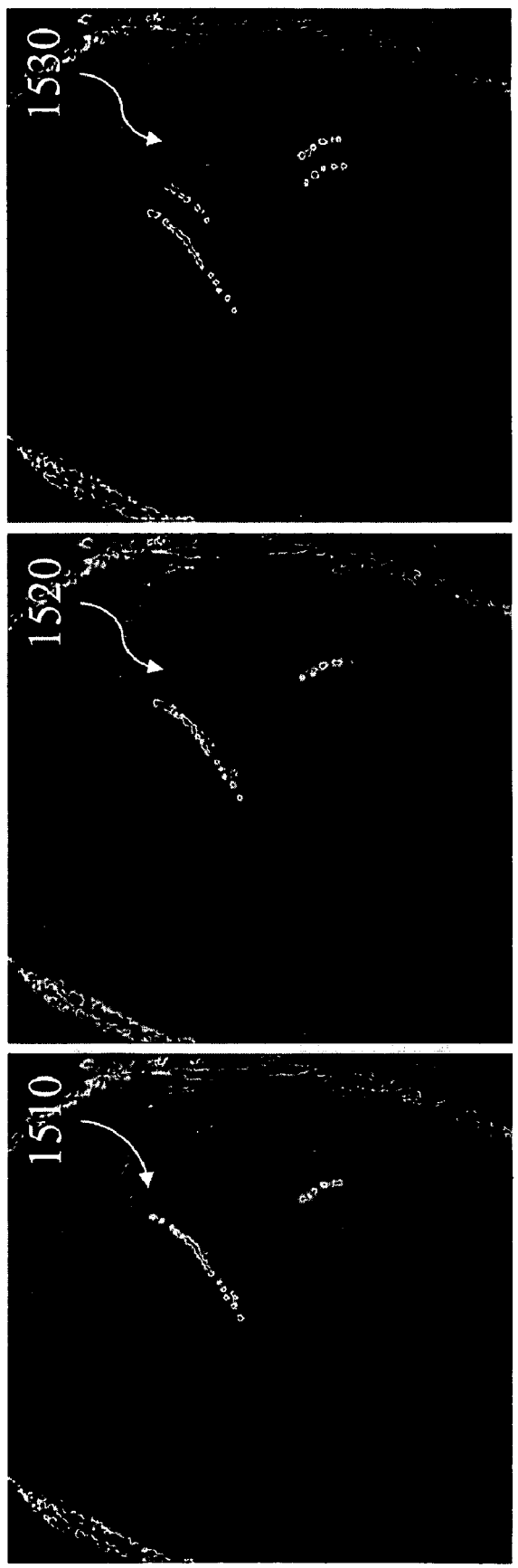
FIG. 17 shows registration results using the data of FIG. 16: (a) using cortical surface landmarkers and PBG, (b) using ICP transforms on the two surfaces, and (c) SurfaceMI registration. The LRS point cloud has been artificially textured to enhance contrast.

Registration results of different methods using the data of FIG. 16 are shown in FIG. 17, where the registration result 1710 is generated by using the cortical surface landmarkers and PBG, the registration result 1720 is generated by using the ICP transforms on the two surfaces, and the registration result 1730 is generated by the SurfaceMI registration. The LRS point cloud has been artificially texture to enhance contrast.

For the second patient, the vessel/sulcal patterns provided enough textural contrast for mutual information to fine-tune the PBG/ICP alignment. While for the third patient the tumor margins abutted the cortical surface. As such a gadolinium pattern of the tumor attenuated the vessel/sulcal texture normally present on the surface. The loss of the texture information resulted in the less accurate registration.

Example 3

Tracking of Surface Deformations

Among other things, the present invention also provides a non-rigid registration capability for the tracking of brain surface deformations with serial range scans.

The data acquisition procedure for tracking brain surface deformations with serial range scans is described above. A laser range scanning device, for example, RealScan3D, was used to intra-operatively capture a 3D topography of the surgical FOV as well surface texture mapping to submillimeter accuracy, which describes the deforming nature of the brain during surgery. This scanner was mounted on a vibration-damped monopod that was brought into and out of the surgical FOV manually. After dural opening, the monopod and scanner were brought into the surgical FOV and the laser scanning extents (left and right margins) were calibrated to cover the width of the craniotomy. A laser stripe was then passed over the brain's surface and range data was collected using the principle of optical triangulation. After acquisition, the scanner and monopod were moved out of the surgical FOV. For the purpose of tracking surface deformations of a targeted region of interest, the RealScan3D was used to sequentially scan the targeted region of interest for acquiring a textured point cloud of the targeted of interest at different times. A 480×640 pixels RGB bitmap image registered to the range data was acquired at the time of scanning.

Figure 18:
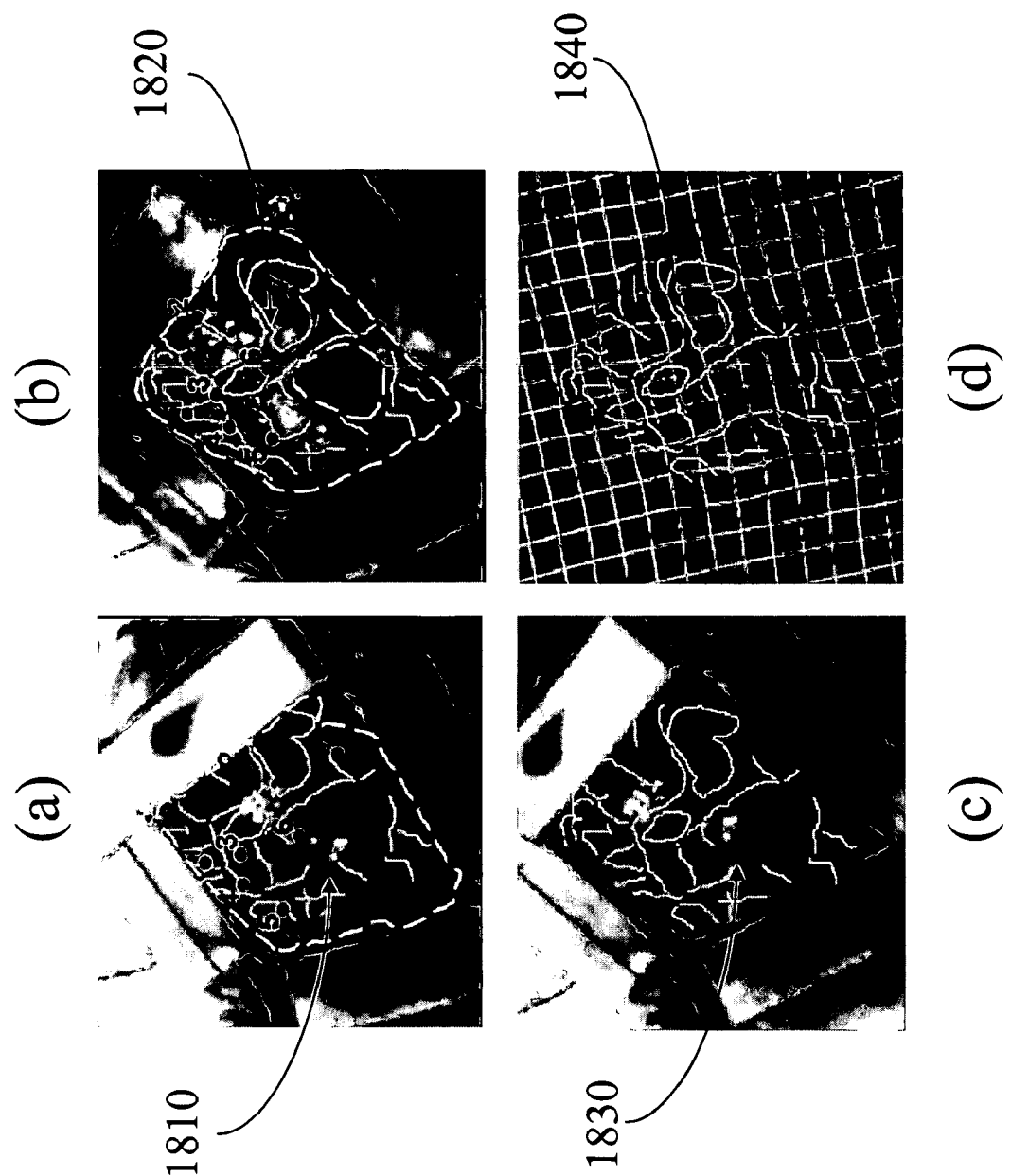
FIG. 18 shows undeformed and deformed images after rigid and non rigid registration for a first in vivo case: (a) a textured point cloud of a targeted region of interest acquired at time $t_1$, (b) a textured point cloud of the targeted region of interest acquired at time $t_2$ later than $t_1$, (c) a result of a rigid body registration of the textured point cloud (a) to the textured point cloud (b), and (d) a result of both a rigid body registration and nonrigid registration of the textured point cloud (a) to the textured point cloud (b).
Figure 19:
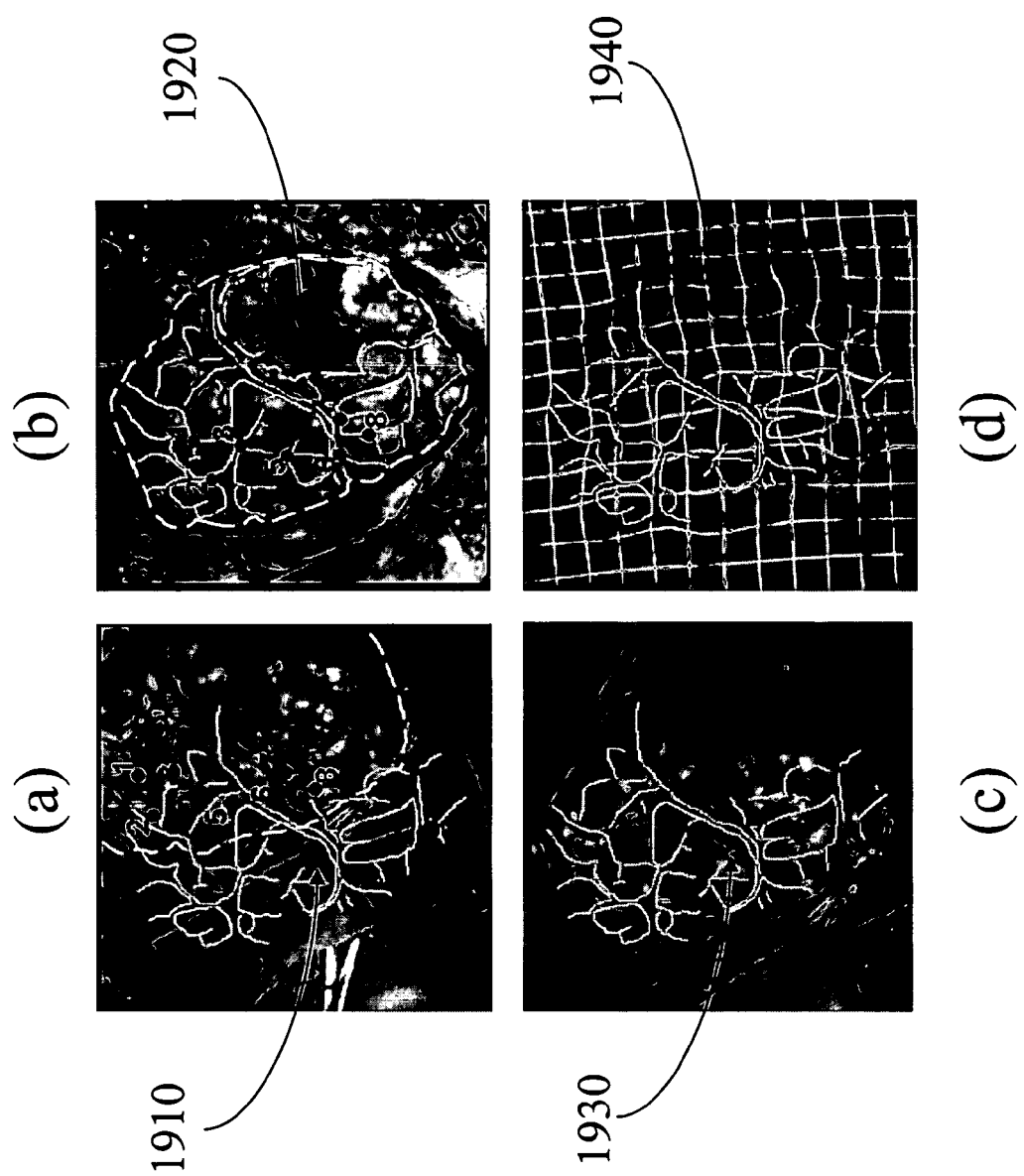
FIG. 19 shows undeformed and deformed images after rigid and non rigid registration for a second in vivo case: (a) a textured point cloud of a targeted region of interest acquired at time $t_1$, (b) a textured point cloud of the targeted region of interest acquired at time $t_2$ later than $t_1$, (c) a result of a rigid body registration of the textured point cloud (a) to the textured point cloud (b), and (d) a result of both a rigid body registration and nonrigid registration of the textured point cloud (a) to the textured point cloud (b).
Figure 20:
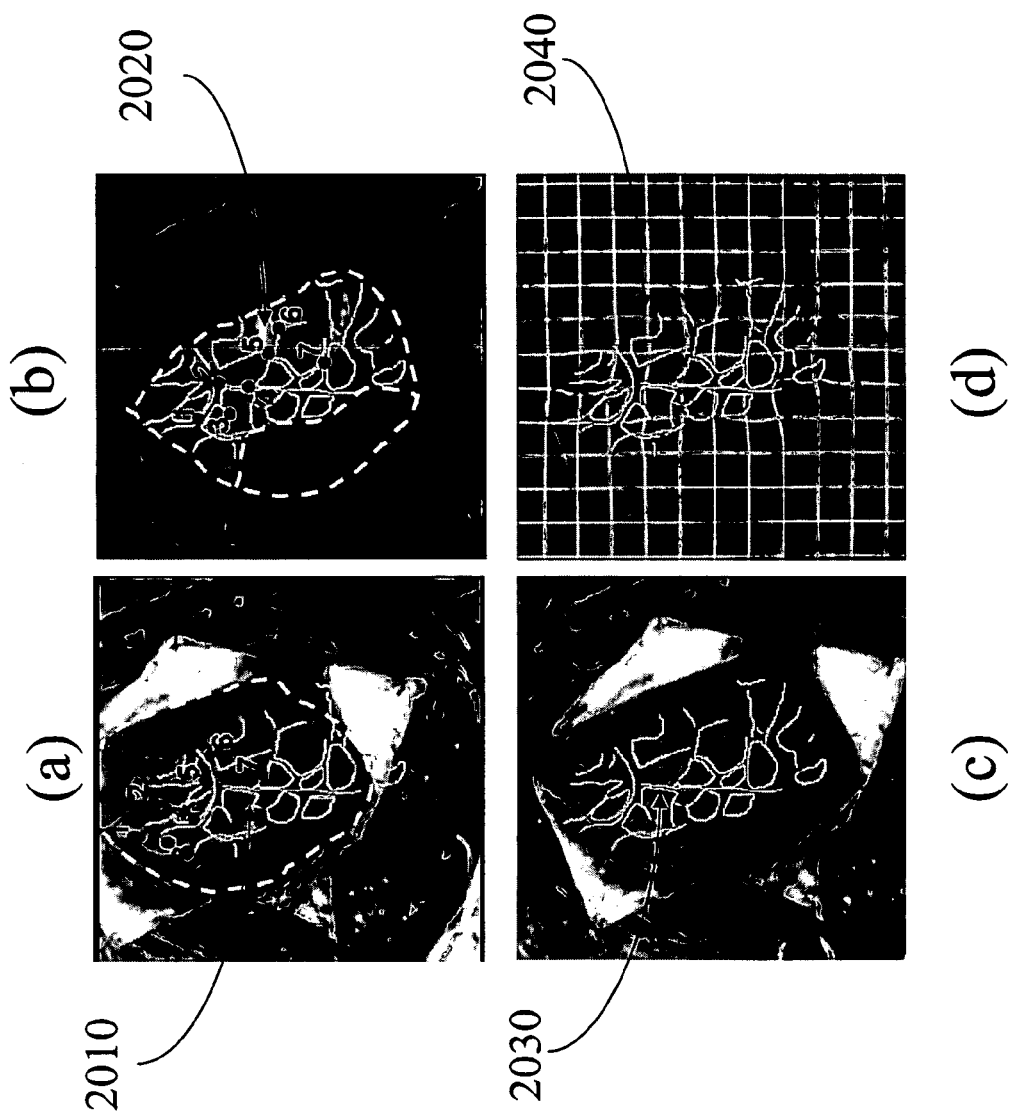
FIG. 20 shows undeformed and deformed images after rigid and non rigid registration for a third in vivo case: (a) a textured point cloud of a targeted region of interest acquired at time $t_1$, (b) a textured point cloud of the targeted region of interest acquired at time $t_2$ later than $t_1$, (c) a result of a rigid body registration of the textured point cloud (a) to the textured point cloud (b), and (d) a result of both a rigid body registration and nonrigid registration of the textured point cloud (a) to the textured point cloud (b).

Referring to FIGS. 18–20, deformations were shown for three in vivo cases, respectively. Each in vivo case corresponded to a surgery in a specific targeted region of interest, and was assigned a number from C1 to C3 as the case identification. For each in vivo case (C1, C2, or C3), as shown in FIGS. 18–20, respectively, figure (a) was a textured point cloud (1810, 1910 or 2010) of the specific targeted region of interest acquired early in the procedure, such as at time $t_1$, by the RealScan3D, figure (b) was a textured point cloud (1820, 1920 or 2020) of the specific targeted region of interest acquired at time $t_2$ later than $t_1$, by the RealScan3D, figure (c) a result (1830, 1930 or 2030) of a rigid body registration of the textured point cloud (1810, 1910 or 2010) of figure (a) to the textured point cloud (1820, 1920 or 2020) of figure (b), and figure (d) was a result (1840, 1940 or 2040) of both a rigid body registration and nonrigid registration of the textured point cloud (1810, 1910 or 2010) of figure (a) to the textured point cloud (1820, 1920 or 2020) of figure (b). As shown in FIGS. 18–20, serial intra-operative images are very different from each other because of large resections (other factors include the appearance and/or disappearance of surgical instruments within the surgical FOV). This presents particular challenges to intensity based registration algorithm. In this exemplary embodiment of the present invention, it was necessary to outline manually targeted region of interest to specify regions over which the transformations was computed. The dashed lines shown in FIGS. 18a, 18b, 19a, 19b, 20a and 20b defined these targeted regions of interest. Homologous landmarks indicated by number 1 to 7 in FIGS. 18a, 18b, 19a, 19b, 20a and 20b and corresponding contours in all these figures were selected and used for quantitative evaluation of the registration results.

Quantitative evaluation was performed as follows. The deformation field $\xi(x_i)$ was used to project the point $x_i$ onto the deformed image to find the deformed points, $$x'_i = \xi(x_i). \tag{3}$$

The error for each pair of points ($\epsilon_i$) was computed as the Euclidian distance between the manually selected points $y_i$ on the deformed image and the corresponding transformed points $x'_i$ as follows, $$\epsilon_i = \|y_i - \xi(x_i)\|. \tag{4}$$

Tables 5–7 present the quantitative results for the in vivo cases C1–C3, respectively. In each of these tables, $d_{in}$ refers to the registration error prior to registration, $\epsilon_r$ is the registration error after rigid body registration, and $\epsilon_{nr}$ is the registration error after both rigid and nonrigid registration. The large error prior to rigid body registration is due to the fact that the scanner was not placed at the same position for the first and second image acquisition.

TABLE 5

Registration error for the in vivo case C1, $d_{in}$, prior to registration, $\epsilon_r$, after rigid body registration, and $\epsilon_{nr}$ after nonrigid registration.

| Landmarks | $d_{in}$ [pixels] | $\epsilon_r$ [pixels] | $\epsilon_{nr}$ [pixels] |
| --- | --- | --- | --- |
| 1 | 16, 13 | 6, 83 | 0, 38 |
| 2 | 33, 54 | 6, 93 | 0, 22 |
| 3 | 19, 31 | 7, 15 | 0, 25 |
| 4 | 14, 21 | 8, 51 | 0, 34 |
| 5 | 17, 46 | 9, 99 | 0, 50 |
| 6 | 25, 55 | 5, 02 | 0, 54 |
| 7 | 36, 77 | 0, 11 | 0, 30 |
| Mean ± SD | 23.28 ± 8.90 | 6.36 ± 3.16 | 0.36 ± 0.12 |

TABLE 6

Registration error for the first in vivo case C2, $d_{in}$, prior to registration, $\epsilon_r$, after rigid body registration, and $\epsilon_{nr}$ after nonrigid registration.

| Landmarks | $d_{in}$ [pixels] | $\epsilon_r$ [pixels] | $\epsilon_{nr}$ [pixels] |
| --- | --- | --- | --- |
| 1 | 66, 29 | 9, 10 | 0, 40 |
| 2 | 65, 80 | 10, 23 | 0, 32 |
| 3 | 64, 82 | 11, 79 | 0, 31 |
| 4 | 62, 80 | 13, 32 | 2, 25 |
| 5 | 61, 22 | 12, 08 | 0, 65 |

TABLE 6-continued

Registration error for the first in vivo case C2, $d_{in}$, prior to registration, $\epsilon_r$, after rigid body registration, and $\epsilon_{nr}$ after nonrigid registration.

| Landmarks | $d_{in}$ [pixels] | $\epsilon_r$ [pixels] | $\epsilon_{nr}$ [pixels] |
|---|---|---|---|
| 6 | 59, 67 | 11, 87 | 0, 51 |
| 7 | 56, 22 | 12, 27 | 0, 25 |
| Mean ± SD | 62.40 ± 3.64 | 11.52 ± 1.40 | 0.67 ± 0.71 |

TABLE 7

Registration error for the first in vivo case C3, $d_{in}$, prior to registration, $\epsilon_r$, after rigid body registration, and $\epsilon_{nr}$ after nonrigid registration.

| Landmarks | $d_{in}$ [pixels] | $\epsilon_r$ [pixels] | $\epsilon_{nr}$ [pixels] |
|---|---|---|---|
| 1 | 38, 60 | 2, 24 | 0, 11 |
| 2 | 39, 29 | 1, 00 | 0, 51 |
| 3 | 40, 52 | 1, 00 | 0, 44 |
| 4 | 42, 72 | 2, 82 | 0, 53 |
| 5 | 40, 52 | 1, 00 | 2, 18 |
| 6 | 41, 98 | 2, 24 | 0, 24 |
| 7 | 39, 56 | 1, 41 | 2, 20 |
| Mean ± SD | 40.46 ± 1.47 | 1.67 ± 0.75 | 0.89 ± 0.90 |

The results shown in FIGS. 18–20 and Table 5–7 indicate that automatic intra-operative tracking of brain motion using a LRS is feasible. Despite large differences in the images due to resection and different viewing angles the approach of the present invention is robust enough to lead to subpixel registration errors.

Further Discussions

In the present invention, among other things, a fast, systematic, non-invasive, non-contact method for registering pre-operative images to the intra-operative patient's cortical surface and for measuring the extent of brain shift during surgery is disclosed. The method, in one embodiment, aligns patient-to-image and tracks the brain for use as input for model-based brain shift compensation strategies. This represents a fundamental advancement for facilitating the possibility of using low-cost computational models to compensate for brain shift during image-guided surgery.

Another important aspect of the SurfaceMI of the present invention is its ability to perform multimodal registration. Within the phantom and clinical experiments, SurfaceMI represents a multimodal registration between CT data and CCD color texture, and MR data and CCD color texture, respectively. This result is quite remarkable and adds impetus for the use of laser-range scanning within the neurosurgical OR environment.

The method according to one embodiment of the present invention in conjunction with the quantitative results provide substantial motivation for using LRS technology within the neurosurgical OR. LRS methods provide rapid detailed characterization of the cortical surface during surgery and can be used as a tool for registration and the eventual measurement of deformation. This versatility will make LRS technology advantageous in pursuing model-updating strategies for the compensation of brain shift during image-guided neurosurgery.

More specifically, phantom experiments are presented that compare traditional point-based and surface-based (ICP) registration methods to a novel registration approach which uses a combined geometric and intensity-based metric (SurfaceMI). The registration approach is a 3D surface alignment technique that begins with an ICP-based initialization followed by a constrained mutual information-based refinement. The algorithm has demonstrated better accuracy with respect to deep tissue targets within the simulated craniotomy region. However, some limitations did appear within the robustness studies whereby a 2% failure rate occurred during phantom registration experiments and clinical trials. In this example shown in FIG. 11, ICP resulted in a better FRE on average with tighter standard deviation than SurfaceMI. The SurfaceMI had produced eight outliers over 500 trials. The areas of local extrema were found near the global extrema and resulted in frustrating numerical optimization methods. These outliers represent a less than 2% failure rate. Furthermore, if the outliers are eliminated from the trial set, the FRE is sharply reduced from mean error of 3.4–2.2 mm. Alternative optimization and multi-resolution methods need to be investigated further to decrease this failure rate [39–41].

One the other hand, for the in vivo cases of the tracking of surface deformations, the algorithm still requires manual intervention to delineate targeted regions of interests over which the transformations are computed but these targeted regions of interests do not need to be delineated very carefully. Further development will address this issue.

While there has been shown several and alternate embodiments of the present invention, it is to be understood that certain changes can be made as would be known to one skilled in the art without departing from the underlying scope of the invention as is discussed and set forth above and below. Furthermore, the embodiments described above are only intended to illustrate the principles of the present invention and are not intended to limit the scope of the invention to the disclosed elements.

LIST OF REFERENCES

[1] C. R. Maurer, J. M. Fitzpatrick, M. Y. Wang, R. L. Galloway, R. J. Maciunas, and G. S. Allen, "Registration of head volume images using implantable fiducial markers," *IEEE Trans. Med. Imag.*, vol. 16, pp. 447–462, April 1997.

[2] J. M. Fitzpatrick, D. L. G. Hill, and C. R. Maurer, *Handbook of Medical Imaging*, M. Sonka and J. M. Fitzpatrick, Eds. Bellingham, Wash.: SPIE Press, 2000, vol. 2, pp. 447–513.

[3] W. E. L. Grimson, G. J. Ettinger, S. J. White, T. Lozano Perez, W. M. Wells, and R. Kikinis, "An automatic registration method for frameless stereotaxy, image guided surgery, and enhanced reality visualization," *IEEE Trans. Med. Imag.*, vol. 15, pp. 129–140, February 1996.

[4] C. R. Maurer, R. J. Maciunas, and J. M. Fitzpatrick, "Registration of head CT images to physical space using a weighted combination of points and surfaces," *IEEE Trans. Med. Imag.*, vol. 17, pp. 753–761, May 1998.

[5] M. A. Audette, K. Siddiqi, and T. M. Peters, "Level-set surface segmentation and fast cortical range image tracking for computing intra-surgical deformations," in *Lecture Notes in Computer Science*. New York: Springer-Verlag, 1999, vol. 1679, Medical Image Computing and Computer Assisted Intervention: MICCAI'99, pp. 788–797.

[6] A. J. Herline, J. L. Herring, J. D. Stefansic, W. C. Chapman, R. L. Galloway, and B. M. Dawant, "Surface registration for use in interactive image-guided liver surgery," in *Lecture Notes in Computer Science*. New York: Springer-Verlag, 1999, vol. 1679, Medical Imaging Computation and Computer-Assisted Intervention: MICCAI'99, pp. 892–899.

[7] A. Raabe, R. Krishnan, R. Wolff, E. Hermann, M. Zimmermann, and V. Seifert, "Laser surface scanning for patient registration in intracranial image-guided surgery," *Neurosurgery*, vol. 50, no. 4, pp. 797–801, 2002.

[8] M. A. Audette, F. P. Ferrie, and T. M. Peters, "An algorithmic overview of surface registration techniques for medical imaging," *Med. Image Anal.*, vol. 4, no. 3, pp. 201–217, 2000.

[9] R. L. Galloway, "The process and development of image-guided procedures," *Annu. Rev. Biomed. Eng.*, vol. 3, pp. 83–108, 2001.

[10] P. J. Kelly, B. Kall, S. Goerss, and F. I. Earnest, "Computer-assisted stereotaxic laser resection of intraaxial brain neoplasms," *J. Neurosurg.*, vol. 64, pp. 427–439, 1988.

[11] H. J. Nauta, "Error assessment during "image guided" and "imaging interactive" stereotactic surgery," *Comput. Med. Imag. Graphics*, vol. 18, no. 4, pp. 279–287, 1994.

[12] D. L. G. Hill, C. R. Maurer, R. J. Maciunas, J. A. Barwise, J. M. Fitzpatrick, and M. Y. Wang, "Measurement of intra-operative brain surface deformation under a craniotomy," *Neurosurgery*, vol. 43, no. 3, pp. 514–526, 1998.

[13] D. W. Roberts, A. Hartov, F. E. Kennedy, M. I. Miga, and K. D. Paulsen, "Intra-operative brain shift and deformation: A quantitative analysis of cortical displacement in 28 cases," *Neurosurgery*, vol. 43, no. 4, pp. 749–758, 1998.

[14] L. D. Lunsford, R. Parrish, and L. Albright, "Intra-operative imaging with a therapeutic computed tomographic scanner," *Neurosurgery*, vol. 15, no. 4, pp. 559–561, 1984.

[15] C. Nimsky, O. Ganslandt, S. Cerny, P. Hastreiter, G. Greiner, and R. Fahlbusch, "Quantification of, visualization of, and compensation for brain shift using intra-operative magnetic resonance imaging," *Neurosurgery*, vol. 47, no. 5, pp. 1070–1079, 2000.

[16] A. Nabavi, P. M. Black, D. T. Gering, C. F. Westin, V. Mehta, R. S. Pergolizzi, M. Ferrant, S. K. Warfield, N. Hata, R. B. Schwartz, W. M. Wells, R. Kikinis, and F. A. Jolesz, "Serial intra-operative magnetic resonance imaging of brain shift," *Neurosurgery*, vol. 48, no. 4, pp. 787–797, 2001.

[17] P. M. Black, T. Moriarty, E. Alexander, P. Stieg, E. J. Woodard, P. L. Gleason, C. H. Martin, R. Kikinis, R. B. Schwartz, and F. A. Jolesz, "Development and implementation of intra-operative magnetic resonance imaging and its neurosurgical applications," *Neurosurgery*, vol. 41, no. 4, pp. 831–842, 1997.

[18] C. Nimsky, O. Ganslandt, H. Kober, M. Buchfelder, and R. Fahlbusch, "Intra-operative magnetic resonance imaging combined with neuronavigation: A new concept," *Neurosurgery*, vol. 48, no. 5, pp. 1082–1091, 2001.

[19] W. E. L. Grimson, R. Kikinis, F. A. Jolesz, and P. M. Black, "Imageguided surgery," *Sci. Amer.*, vol. 280, no. 6, pp. 62–69, 1999.

[20] C. Nimsky, O. Ganslandt, P. Hastreiter, and R. Fahlbusch, "Intra-operative compensation for brain shift," *Surg. Neurol.*, vol. 56, no. 6, pp. 357–364, 2001.

[21] M. Knauth, N. Aras, C. R. Wirtz, A. Dorfler, T. Engelhorn, and K. Sartor, "Surgically induced intracranial contrast enhancement: Potential source of diagnostic error in intra-operative mr imaging," *Amer. J. Neuroradiol.*, vol. 20, no. 8, pp. 1547–1553, 1999.

[22] G. R. Sutherland, T. Kaibara, C. Wallace, B. Tomanek, and M. Richter, "Intra-operative assessment of aneurysm clipping using magnetic resonance angiography and diffusion-weighted imaging: Technical case report," *Neurosurgery*, vol. 50, no. 4, pp. 893–897, 2002.

[23] R. D. Bucholz, D. D. Yeh, J. Trobaugh, L. L. McDurmont, C. D. Sturm, C. Baumann, J. M. Henderson, A. Levy, and P. Kessman, "The correction of stereotactic inaccuracy caused by brain shift using an intra-operative ultrasound device," in *Lecture Notes in Computer Science*. New York: Springer-Verlag, 1997, vol. 1205, CVRMEDL: MRCAS'97, pp. 459–466.

[24] D. G. Gobbi, R. M. Comeau, and T. M. Peters, "Ultrasound/mri overlay with image warping for neurosurgery," in *Lecture Notes in Computer Science*. New York: Springer-Verlag, 2000, vol. 1935, Medical Image Computing and Computer-Assisted Intervention: MICCAI'00, pp. 106–114.

[25] A. Gronningsaeter, A. Kleven, S. Ommedal, T. E. Aarseth, T. Lie, F. Lindseth, T. Lango, and G. Unsgard, "Sonowand, an ultrasound-based neuronavigation system," *Neurosurgery*, vol. 47, no. 6, pp. 1373–1379, 2000.

[26] F. Lindseth, T. Lango, J. Bang, and T. A. N. Hernes, "Accuracy evaluation of a 3D ultrasound-based neuronavigation system," *Comput. Assist. Surg.*, vol. 7, pp. 197–222, 2002.

[27] D. W. Roberts, M. I. Miga, A. Hartov, S. Eisner, J. M. Lemery, F. E. Kennedy, and K. D. Paulsen, "Intra-operatively updated neuroimaging using brain modeling and sparse data," *Neurosurgery*, vol. 45, no. 5, pp. 1199–1206, 1999.

[28] M. I. Miga, K. D. Paulsen, J. M. Lemery, S. D. Eisner, A. Hartov, F. E. Kennedy, and D. W. Roberts, "Model-updated image guidance: Initial clinical experiences with gravity-induced brain deformation," *IEEE Trans. Med. Imag.*, vol. 18, pp. 866–874, October 1999.

[29] M. I. Miga, K. D. Paulsen, F. E. Kennedy, P. J. Hoopes, A. Hartov, and D. W. Roberts, "In vivo analysis of heterogeneous brain deformation computations for model-updated image guidance," *Comput. Methods Biomech. Biomed. Eng.*, vol. 3, no. 2, pp. 129–146, 2000.

[30] R. Bajcsy, R. Lieberson, and M. Reivich, "A computerized system for the elastic matching of deformed radiographic images to idealized atlas images," *J. Comput. Assist. Tomogr.*, vol. 7, no. 4, pp. 618–625, 1983.

[31] J. C. Gee, D. R. Haynor, L. LeBriquer, and R. K. Bajcsy, "Advances in elastic matching theory and its implementation," in *Lecture Notes in Computer Science*. New York: Springer-Verlag, 1997, vol. 1205, CVRMed: MRCAS'97, pp. 63–72.

[32] G. E. Christensen, R. D. Rabbitt, and M. I. Miller, "3D brain mapping using a deformable neuroanatomy," *Phys. Med. Biol.*, vol. 39, no. 3, pp. 609–618, 1994.

[33] S. Nakajima, H. Atsumi, R. Kikinis, T. M. Moriarty, D. C. Metcalf, F. A. Jolesz, and P. M. Black, "Use of cortical surface vessel registration for image-guided neurosurgery," *Neurosurgery*, vol. 40, no. 6, pp. 1201–1208, 1997.

[34] C. Studholme, D. L. G. Hill, and D. J. Hawkes, "An overlap invariant entropy measure of 3d medical image alignment," *Pattern Recognit.*, vol. 32, no. 1, pp. 71–86, 1999.

[35] W. H. Press, S. A. Teukolsky, W. T. Vetterling, and B. P. Flannery, *Numerical Recipes in C: The Art of Scientific Computing*, 2nd ed. New York, N.Y.: Cambridge Univ. Press, 1992.

[36] V. R. Mandava, "Three-dimensional multimodal image registration using implanted markers," Ph.D. dissertation, Vanderbilt Univ., Nashville, Tenn., December 1991.

[37] V. R. Mandava et al., "Registration of multimodal volume head images via attached markers," in *Proc. SPIE Medical Imaging IV: Image Processing*, vol. 1652, 1992, pp. 271–282.

[38] B. Rosner, *Fundamentals of Biostatistics*, 4th ed. Belmont, Calif.: Duxbury, 1995.

[39] F. Glover, "Tabu search: A tutorial," *Interfaces*, vol. 20, no. 4, pp. 74–94, 1990.

[40] A. Hertz, E. Taillard, and D. de Werra, *Local Search in Combinatorial Optimization*. New York: Wiley, 1997.

[41] D. J. Hawkes, C. Studholme, and D. L. Hill, "Accuracy, precision, and robustness of fully automated 3D neuro-image registration by multi-resolution optimization of mutual information (MOMI)," *Radiology*, vol. 205, pp. 111–111, 1997.

What is claimed is:

1. A method of registering an image volume of a brain of a living subject to a cortical surface of at least one targeted region of the brain of the living subject, comprising the steps of:
   a. pro-operatively acquiring the image volume from the brain of the living subject;
   b. generating a grayscale encoded brain surface from the acquired image volume;
   c. intra-operatively obtaining a textured point cloud of the cortical surface of the at least one targeted region of the brain of the living subject;
   d. aligning the grayscale-encoded brain surface to the textured point cloud of the conical surface so as to register the image volume of the brain with respect to the cortical surface of the at least one targeted region of the brain,
   wherein the textured point cloud contains intensity patterns representing sulcal-gyrus differences and contrast-enhanced vasculature related to the cortical surface of the at least one targeted region of the brain of the living subject; and
   e. generating an image of the registered image volume.

2. The method of claim 1, wherein the image volume of the brain of the living subject comprises image data with respect to the brain surface geometry.

3. The method of claim 2, wherein the image data with respect to the brain surface geometry is obtained through the use of at least one of positron emission tomography, electroencephalography, computer tomography, functional magnetic resonance imaging and magnetic resonance imaging.

4. The method of claim 1, wherein the step of generating a grayscale encoded brain surface comprises the steps of:
   a. segmenting the acquired image volume of the brain of the living subject;
   b. extracting a point cloud representation of the brain surface geometry from the segmented image volume; and
   c. performing a ray-casting and voxel intensity avenging on the point cloud representation so as to generate a grayscale encoded brain surface tat contains intensity patterns representing sulcal-gyrus differences and contrast-enhanced vasculature.

5. The method of claim 1, wherein the step of obtaining a textured paint cloud of the cortical surface is performed with an optical device that is capable of obtaining frequency, intensity and geometric data with respect to the cortical surface simultaneously.

6. The method of claim 5, wherein the optical device is a laser range scanner.

7. The method of claim 6, wherein the step of intra-operatively obtaining a textured point cloud of the cortical surface comprises the steps of:
   b. optically scanning an exposed brain surface of the living subject during surgery with the Laser range scanner;
   c. capturing surface-reflected light from the brain surface of the living subject;
   d. acquiring a point cloud representation of the geometry of the cortical surface from the captured surface-reflected light; and
   e. color-encoding the acquired point cloud representation with intensity values of a field of view so as to obtain a textured point cloud of the cortical surface of the at least one targeted region of the brain.

8. The method of claim 1, wherein the step of aligning the grayscale-encoded brain surface to the textured point cloud of the cortical surface comprises the steps of:
   a. registering the grayscale-encoded brain surface of the brain to the textured point cloud of the cortical surface of the targeted region of the brain using an iterative closest point algorithm; and
   b. optimizing the grayscale-encoded brain surface of the brain to the textured point cloud of the cortical surface of the targeted region of the brain using normalized mutual information.

9. The method of claim 8, wherein the registering step comprises the steps of:
   a. pairing corresponding points from the grayscale-encoded brain surface of the brain and the textured point cloud of the cortical surface of the targeted region of the brain according to a closest distance metric;
   b. executing a point-based registration;
   c. updating the closest distance metric accordingly; and
   d. repeating steps (a)–(c) until a disparity function d satisfies a specified tolerance, wherein the disparity function d has the form of:

$$d = \frac{1}{N}\sum_{j}^{N} \|y_j - T(x_j)\|^2$$

wherein $T(x_j)$ represents a rigid transformation of N points on a source surface to corresponding points on a target surface, $y_j$.

10. The method of claim 9, wherein the optimizing step comprises the steps of:
   a. choosing a normalized mutual information in the form of $$NMI(x, y) = \frac{H(x) + H(y)}{H(x, y)}$$

wherein $H(x)$ and $H(x, y)$ are the marginal and joint entropies of the point clouds, respectively;
   b. using the closest distance metric to determine proper intensity correspondence among a source surface and a target surface;
   c. fitting a spherical geometry to reduce the registration degrees of freedom; and
   d. optimizing the normalized mutual information using an iterative procedure.

11. A cortical surface registration procedure related to a diagnostic or surgical procedure, comprising the steps of:

(i) pre-operatively obtaining a first textured point cloud of the cortical surface of a targeted region of a brain of a living subject;
(ii) intra-operatively obtaining optically a second textured point cloud of the cortical surface of the brain of the living subject;
(iii) aligning the first textured point cloud of the cortical surface to the second textured point cloud of the cortical surface so as to register images of the brain of the living subject to the cortical surface of the living subject; and
(iv) generating an image of the registered image volume. wherein the step of pre-operatively obtaining a first textured point cloud comprises the steps of:
a. pro-operatively acquiring an image volume from the brain of the living subject;
b. segmenting the acquired image volume;
c. extracting a point cloud representation of the brain surface geometry from the segmented image volume;
d. performing a ray-casting and voxel intensity averaging on the point cloud representation so as to generate a grayscale encoded brain surface that contains intensity patterns representing sulcal-gyrus differences and contrast-enhanced vasculature; and
e. obtaining the first point cloud from the grayscale encoded brain surface.

12. The procedure of claim 11, wherein the image volume of the brain of the living subject comprises image data with respect to the brain surface geometry.

13. The procedure of claim 12, wherein the image data with respect to the brain surface geometry is obtained through the use of at least one of positron emission tomography, electroencephalography, computer tomography, functional magnetic resonance imaging and magnetic resonance imaging.

\* \* \* \* \*